(12) United States Patent
Ferrante et al.

(10) Patent No.: US 6,376,688 B1
(45) Date of Patent: Apr. 23, 2002

(54) MODIFIED POLYUNSATURATED FATTY ACIDS

(75) Inventors: Antonio Ferrante, Mount Osmond; Alfred Poulos, Kensington Gardens; Christopher John Easton, Weetangera; Michael Joseph Pitt, Garran; Thomas Alistair Robertson, Aranda; Deborah Ann Rathjen, Sheidow Park, all of (AU)

(73) Assignee: Peptide Technology Limited, New South Wales (AU)

( * ) Notice: Subject to any disclaimer, the term of this patent is extended or adjusted under 35 U.S.C. 154(b) by 0 days.

(21) Appl. No.: 08/817,430

(22) PCT Filed: Oct. 13, 1995

(86) PCT No.: PCT/AU95/00677

§ 371 Date: May 29, 1997

§ 102(e) Date: May 29, 1997

(87) PCT Pub. No.: WO96/11908

PCT Pub. Date: Apr. 25, 1996

(30) Foreign Application Priority Data

Oct. 13, 1994 (AU) .............................. PM 8781
Oct. 26, 1994 (AU) .................................. 9066

(51) Int. Cl.⁷ .......................... C07B 45/00; C07C 51/00; A01N 37/00
(52) U.S. Cl. ....................... 554/101; 554/154; 554/213; 554/223; 554/224; 514/558; 514/560; 514/885; 514/895
(58) Field of Search ................................ 554/223, 224, 554/101, 213, 154; 514/558, 560, 895, 885

(56) References Cited

FOREIGN PATENT DOCUMENTS

| EP | 87113474 | 9/1987 |
| EP | 260655 | * 3/1988 |
| EP | 89305478 | 5/1989 |
| EP | 345038 | * 12/1989 |
| WO | PCT/AU92/00313 | 6/1992 |
| WO | PCT/IB94/00085 | 3/1994 |
| WO | PCT/AU94/00607 | 10/1994 |

OTHER PUBLICATIONS

Schackey et al., Journal of Lipid Research, vol. 31, pp. 801–810, 1990.*
Clemens von Schacky, "Platelet–neutrophil interactions. 12S, 20–and 5S, 12S–. . . " (1990), Journal of Lipid Research, vol. 31, p. 801–810.
Yael Bromberg, "Oxidative Metabolism of Lymphokine Activated . . . " (1983), Interleukins, Lymphokines, and Cytokines, pp. 561–568.
Lakshmi, M. Kumaratilake, "Antimalarial Properties of n–3 and n–6 Polyunsaturated Fatty Acids: . . . " Antimalarial Properties of Polyunsaturated Fatty Acids, 1992, vol. 89, p. 961–967.
Abraham Demoz, "Modulation of Plasma and Hepatic Oxidative Status and Changes . . . " Elsevier Science, (1994), pp. 238–244.
F. Roden PCT/95/00677, Section B2.
Ri, Bunsho, "Anti–inflammatory agents containing [5Z, 8Z, 11 . . . ", (1993), Pharmacology, vol. 119, 19567la.

* cited by examiner

*Primary Examiner*—Deborah D. Carr
(74) *Attorney, Agent, or Firm*—Nixon & Vanderhye

(57) ABSTRACT

The present invention provides polyunsaturated fatty acid compounds having antimalarial and/or neutrophil stimulatory activity. The polyunsaturated fatty acids contain 18–25 carbons and 1–6 double bonds and are characterized in that they have one or two substitutions selected from the group consisting of β oxa, γ oxa, β thia and γ thia. It is also preferred that the polyunsaturated fatty acid compound includes a further substitution selected from the group consisting of hydroxy, hydroperoxy, peroxy, carboxymethyl substitutions or attached to an amino acid. The invention also provides a method of producing an unsaturated oxa substituted fatty acid comprising reacting an unsaturated fatty acid alcohol with a carbene that is inserted in the OH bond of the alcohol, the invention further provides a method of treating inflammation with a composition comprising at least one hydroxy, hydroperoxy or peroxy derivative of a polyunsaturated fatty acid having a $C_{18-24}$ carbon chain and 1–6 cis or trans double bonds.

22 Claims, 14 Drawing Sheets

MODIFIED POLYUNSATURATED FATTY ACIDS

This application is a 371 of PCT/AU95/00677 filed Oct. 13, 1995.

The present invention relates to new polyunsaturated fatty acids having antimalarial activity and/or neutrophil stimulatory activity. The present invention further relates to a group of modified polyunsaturated fatty acids which have the ability to suppress cytokine production and cytokine action. Such fatty acids have enhanced stability when compared to naturally occurring polyunsaturated fatty acids. The present invention further relates to compositions including the polyunsaturated fatty acids as the active ingredient and methods of anti-malarial, anti-infective of anti-inflammatory treatment or prevention involving the administration of this composition.

BACKGROUND OF THE INVENTION

Over half of the world's population is at risk from malaria, with about 500 million acute infections and approximately 1 million deaths recorded each year. (Tropical Diseases Progress in International Research, 1987–1988. Ninth Programme Report, UNDP/World Bank/WHO, Geneva, 43–49: Stevenson MM Preface In: Stevenson MM. Ed. Malaria: Host responses to Infection, CRC Press, Inc). The use of antimalarial drugs is associated with major problems because of increased resistance and toxic side-effects. Most currently used antimalarials are unsuitable for use in children (most at risk of potentially fatal cerebral malaria), pregnant women and the aged.

Inflammation may be caused by bacteria, viruses and/or other infective agents, opportunistic infections (which may be consequent on an immunodepressed state, for example resulting from cancer or therapy, particularly cytotoxic drug therapy or radiotherapy), autoimmunity of otherwise. Septic shock is an illustration of a disease involving inflammation. Many of the clinical features of Gram-negative septic shock may be reproduced in animals by the administration of LPS to animals can prompt severe metabolic and physiological changes which can lead to death. Associated with the injection of LPS is the extensive production of pro-inflammatory cytokines such as tumour necrosis factor alpha [TNFα]. Cachexia, which is characteristic of chronic exposure to TNF or interleukin-6, is a common symptom of advanced malignancy and severe infection. It is characterised by abnormal protein and glucose metabolism and body wasting. Chronic administration of TNF IL-1 in mice, rats and/or humans cause anorexia, weight loss and depletion of body lipid and protein within 7 to 10 days (Cerami et al. 1985, Immunol. Lett. 11, 173: Fong et al, 1989J. Exp. Med. 170, 1627, Moldawer et al. Am. J. Phusiol., 254 G450–G456, 1988: Fong et am. Am. J Physiol, 256, R659–R665 (1989): McCarthy et al. Am. J. Clin. Nature, 42, 1179–1182, 1982). TNF levels have been measured in patients with cancer and chronic disease associated with cachexia.

TNFα and IL-1, with their common functional activities such as pyrogenicity, somnogenicity and being mediators of inflammation, have been implicated in the pathology of other diseases associated with chronic inflammation apart from toxic shock and cancer-related cachexia. TNF has been detected in synovial fluid in patients with both rheumatoid and reactive arthritis and in the serum of patients with rheumatoid arthritis (Saxne et en. 1988, Arthrit. Rheumat. 31, 1041). Raised levels of TNF have been detected in renal transplant patients during acute rejection episodes (Maury and Teppo 1987, J. Exp. Med. 166, 1132). In animals, TNF has been shown to be involved in the pathogenesis of graft-versus-host disease in skin and gut following allogenic marrow transplantation.

Administration of a rabbit anti-murine TNF antibody was shown to prevent the histological changes associated with graft-versus-host disease and to reduce mortality (Piquet et en. 1987, J. Exp. Med. 166, 1220). TNF has also been shown to contribute significantly to the pathology of malaria (Clark et al. 1987, Am. J. Pathol. 129, 192–199). Further, elevated serum lebvels of TNF have been reported in malaria patients (Scuderi et al. 1986, Lancet 2, 1364–1365).

Multiple sclerosis (MS) is a chronic demyelinating disease of the central nervous system and is the commonest chronic neutroligical disease of young adults. The incidence of MS and its pattern of distribution have been unchanged for decades. The disease remains essentially untreatable.

MS usually affects multiple areas of white matter in the central nervous system (CNS), most frequently, the preventricual white matter, brainstem, spinal cord and the optic nerves. The primary process destroys myelin sheaths and eventually kills oligodendrocytes creating the characteristic plaque of MS.

The early development of the plaque is characterised by the development of perivascular inflammation followed by the migration of lymphocytes, plasma cells and macrophages into the lesion. This is followed by astrocyte gliosis and the attempts of demyelination by oligodendrocytes. The plaque is surrounded by lymphocytes. Anti-T cell agents such as anti-CD4 treatment are effective. Such agents inhibit the proliferation of T-cells.

Although the aetiology of MS is still unknown, the focus of research efforts that have led to plausible hypotheses have been those of immune dysregulation including autoimmunity and genetic predisposition, both of which may play a role in the actual development of disease. Both TNFα (lymphotoxin) and TNFα are thought to play a role in the pathophysiology.

Multiple immunological abnormalities are reproducibly found in patients in the acute stage of the disease. The synthesis of immunoglobulins, although normal in the periphery, is increased in the central nervous system and the antibodies produced have a characteristic banding pattern. The antigenic, specificity of these antibodies is not known and it is unclear whether they have a role to play in the progression of the disease.

Various stressors known to activate the immune system such as viral infection or surgery can also produce an exacerbation of MS. Other activators such as γ-interferon produce similar effects when administered. In addition, immunosuppressive anti-inflammatory therapy with corticosteroids for example, can produce modest remission or at least palliation for short periods of time.

Myelopathy, a disorder of the spinal cord, can have many different aetiologies, most of which are mediated by inflammation, including the following:

Neurosyphillis:

$b_{12}$ or folate deficiency:

sarcoidosis:

transverse myelitis:

arachidonitis:

cervical spondylitis:

motor neuron disease:

neurofibromatosis:
spinal cord compression from tumour, disc or arthritis:
lupus erythematosus of the spinal cord: and
viral encephalomyelitis Chronic inflammation or, as more commonly known, chronic immune system activation occurs in response to persistent antigen whose origin may be exogenous or may result from an autoimmune state. Such chronic inflammation results in local tissue destruction and depending upon the type of inflammation can result in systemic effects due to the sustained production of inflammatory mediators. Such inflammatory mediators include the cytokines which are soluble mediators produced by activated lymphocytes and macrophages and effect cellular communication and physiological response. Chronic immune activation can occur as a result of infectious disease, such as chronic fatigue syndrome or toxic shock syndrome or through autoimmune mechanisms resulting in such conditions as rheumatoid arthritis, inflammatory bowel disease, Crohns Disease and other diseases such as graft versus host disease.

Rheumatoid arthritis [Marrow et al. I "Autoimmune Rheumatic Disease", *Blackwell Scientific Publ.* Oxford, UK, Chapter 4 pp148–207 (1987)] is a disease characterised by chronic inflammation and erosion of joints that may affect up to 3% of the population, including children. Symptoms of rheumatoid arthritis include morning stiffness, swelling and pain upon motion in at lease one joint and joint swelling. Non-specific symptoms including lethargy, anorexia and weakness as well as fever and lymphadenopathy (characteristic of immune activation) may antedate joint involvement. Extra-articular manifestations of rheumatoid arthritis include vasculitis, cataracts, uveitis, interstitial fibrosis, pericarditis and myocarditis, peripheral neuropathy, myeloid deposits, chronic anaemia and subcutaneous and pulmonary nodules.

Genetic factors and infectious agents including bacteria, fungi, mycoplasmas and viruses have been associated with the development of rheumatoid arthritis. Mild rheumatoid arthritis may be treated with non-steroidal anti-inflammatory drugs while severe cases require systemic corticosteroids, anti-metabolites or cytotoxic agents. Experimentally, anti-CD4 monoclonal antibodies and anti-TNFα antibodies have been used to treat rheumatoid arthritis (Horneff et al, Cytokine 3 266–267 (1991): Horneff et al. Arth. Rheum. 34 129–140 (1991) and Shoenfeld et al, Clin. Exp. Rheum. 9, 663–673 (1991). Williams et al. 1992 PNAS 89, 9784).

Inflammatory bowel disease (IBD) and Crohns disease are chronic inflammatory conditions that fulfil some of the criteria of an autoimmune disease [Snook, Gut 31 961–963 (1991)]. Inflammation and tissue damage involves the recruitment and activation of neutrophils, macrophages and lymphocytes [MacDermott et al. Adv. Immunol. 42 285–328 (1988)] which generate cytokines and proinflammatory molecules such as prostaglandins and leukotrienes [MacDermott, Mt. Sinai J. Med. 57 273–278 (1990)]. As a result of chronic activation of immunocompetent cells, IL-1, IL-6[Starter, Immunol. Res. 10 273–278 (1990); Fiocchi, Immunol. Res. 10 239–248 (1991)] and TNFα [MacDermott, Mt. Sinai J. Med. 57 273–278 (1990)] are all elevated in IBD and Crohns Disease patients.

Drugs used to treat IBD and Crohns Disease include anti-inflammatory agents such as sulphasalazine (5-ASA) corticosteroids, cyclosporin A and azathiprine (Hanauer. Scand. J. Gastroenterol, 25 (Supl. 175) 97–106 (1990); Peppercorn. Annal, Intern, Med. 112 50–60 (1990)). Experimentally, anti-CD4 and anti-TNF monoclonal antibodies have been used to successfully treat ulcerative colitis (Emmerich et al. Lancet 338 570–571 (1991)).

Whilst a host may react against a genetically incompatible graft producing a host-versus-graft response, an immunocompetent graft (such as bone marrow or intestinal tissue) may react against the host resulting in graft-versus-host disease. These reactions are mediated by allogenic responses directed against a foreign MHC molecule and are mimicked in vitro by the mixed lymphocyte reaction (MLR). Graft/host interactions result in chronic inflammation surrounding the grafted tissue with an increase in markers of immune activation such as are seen in ADS (Grant. Immunol. Today 12 171–172 (1991)). Treatment of the graft/host interactions currently include either azathioprine, cyclosporin A or methylprednisone and, more recently, rapamycin (Spekowski et al. Transplantation 53 258 . 264 (1992); Huber et al. Bibliotheca Cardiologica. 43 103–110 (1988)). Monoclonal antibodies specific for CD3 (Wissing et al. Clin Exp Immunol. 83 333–337 (1991)), CD4 (Reinke et al. Lancet 338 702–703 (1991)) and TNFα have been used experimentally to inhibit graft/host reactions.

as mentioned above PUFAs have a range of useful biological activities (see for example International Patent Application Nos. WO 93/00084 and WO 95/09622 and the references cited therein). Unfortunately, due to their limited stability in vivo. PUFAs have not achieved widespread use as therapeutic agents. The present inventors have developed substituted PUFAs which while retaining biological activity have increased stability in vivo i.e. slower metabolic turnover. These new polyunsaturated fatty acid (PUFA) compounds have direct antimalarial activity. In addition to their direct antimalarial activity, the novel PUFA activate human neutrophils causing release of granule contents, and exhibit synergy with TNF in the production of superoxide. Activation of human neutrophils by the PUFA results in enhanced ability of these cells to kill malaria parasite (*P. falciparum*) within red blood cells and also the bacteria *Staphylococcus aureus*.

Further, the present inventors have also found that certain polyunsaturated fatty acids and novel polyunsaturated fatty acids and their hydroxy and hydroperoxy derivatives suppress production of cytokines.

These new PUFAs include at least one β oxa, β thia, γ oxa or γ thia substitution. While saturated β-oxa fatty acids can be obtained using the standard procedure for either synthesis, by reaction of alkyl halides with the dianions of α-hydroxy acids or by treating α-halo acids with deprotonated alcohols, the unsaturated β-oxa fatty acids of the present invention are not accessible using normal methods. Attempts to obtain the unsaturated compounds in this manner lead only to decomposition products, resulting from undesirable side reactions at the olefinic and allylic carbons.

In a recent variation of the standard procedure, saturated β-oxa fatty acids have been obtained through nucleophilic substitution reactions under less vigorous conditions, by treating diazoacetates, activated by complexation with boron trifluoride etherate, with alcohols. However, boron trifluoride etherate is known to cause isomerization of alkenes and it is therefore unsuitable for use in the synthesis of unsaturated β-oxa fatty acids.

DESCRIPTION OF THE INVENTION

The present inventors have now found that unsaturated β-oxa fatty acids can be obtained, in good yields, by insertion of carbenes in the O—H bond of alcohols. There is no complication from other carbene insertion reactions and, of particular significance, the olefinic moieties are unaffected under the reaction conditions.

The carbene can be generated from the corresponding diazo acetate or diazo alkane, by treatment with a catalyst such as a rhodium salt. Reaction of the carbene with the complementary alcohol, which is either a derivative of α-hydroxy acetic acid or an unsaturated fatty alcohol affords the unsaturated β-oxa fatty acid. In a preferred embodiment the alcohols are those obtained by reduction of naturally occurring unsaturated fatty acids or the corresponding esters, and reaction with an ester of diazo acetic acid affords the unsaturated β-oxa fatty acid.

The present inventors have also shown that both β-oxa and β-thia substituted fatty acids are unable to undergo β oxidation. In addition certain of the novel compounds display other properties which differ from those of natural PUFA including enhanced solubility, varied oxidation reduction potentials and different charge and polarity.

Accordingly, in a first aspect the present invention consists in a polyunsaturated fatty acid compound having antimalarial and/or neutrophil stimulatory activity, the polyunsaturated fatty acid containing 18–25 carbons and 1–6 double bonds and wherein the polyunsaturated fatty acid compound has one or two substitutions selected from the group consisting of β oxa. γ oxa, β thia and γ thia.

In a preferred embodiment of the present invention the polyunsaturated fatty acid compound includes a further substitution selected from the group consisting of hydroxy, hydroperoxy, peroxy and carboxymethyl substitutions. In another embodiment the substituted fatty acid is covalently attached to an amino acid.

In a further preferred embodiment of the present invention the polyunsaturated fatty acid compound contains 20–25 carbon atoms and 3–6 double bonds and is preferably an n-3 to n-6 fatty acid.

In another preferred embodiment of the present invention the polyunsaturated fatty acid compound is 21 carbons with 3–4 double bonds containing a β oxa or β thia substitution, 22 carbon atoms with 3–4 double bonds containing a γ thia or β oxa substitution. 23 carbons with 3–4 double bonds containing a β thia substitution. 24 carbons with 3–4 double bonds containing a γ thia substitution. 25 carbons with 3–6 double bonds containing a β oxa substitution. 25 carbons with 3–6 double bonds containing a β thia substitution, or 23 carbons, 3–6 double bonds, β thia and α-carboxymethyl group.

In yet another preferred embodiment of the present invention the polyunsaturated fatty acid compound has a ω hydroxy substitution.

In another preferred form of the invention the polyunsaturated fatty acid compound is attached to an amino acid, preferably an aspartic acid or glycine.

In a second aspect the present invention consists in a method of producing an unsaturated oxa substituted fatty acid comprising reacting an unsaturated fatty acid alcohol with a carbene such that the carbene is inserted in the O—H bond of the alcohol.

In a preferred embodiment of this aspect of the present invention the unsaturated fatty acid alcohol contains 18–25 carbon atoms and 1–6 double bonds.

In a further preferred embodiment of this aspect of the present invention the carbene is synthesized via rhodium acetate catalysed of a diazo compound.

In another preferred embodiment of this aspect of the present invention an unsaturated β oxa substituted fatty acid is produced.

In a third aspect the present invention consists in a method of treating inflammation in a subject, the method comprising administering to the subject a therapeutically effective amount of an anti-inflammatory composition comprising at least one hydroxy, hydroperoxy, or peroxy derivative of a polyunsaturated fatty acid having a carbon chain of 18 to 24 carbon atoms and having 1–6 cis or trans double bonds.

In a preferred embodiment of this aspect of the present invention the poly unsaturated fatty acid may contain oxygen or sulphur atoms within the carbon chains as oxa or thia derivatives.

In a further preferred embodiment of this aspect of the present invention the polyunsaturated fatty acid is selected from the group consisting of the C20:4n-6 (5, 8, 11, 14-eicosatetraenoc acid). C20:5N-3 (5, 8, 11, 14, 17-eicosapentaenoic). C22:6n-3 (4, 7, 10, 13, 16, 19-docosahexaenoic acid) and arachidonic acid.

Neutrophil/macrophage stimulatory agents may have application in the treatment of other infections including Candida sp. Trypanosoma, Schistosomiasis, Tuberculosis, viruses eg herpes, Sindbis virus, Legionella, Listeriosis, Pneumocystsis, Pseudomonas. They would also be useful as adjunct therapy in immunocomporomised individuals including those undergoing cancer chemotherapy and transplant recipients and burns patients. In addition others, so called normal individuals may also be treated eg the aged, children under 2, alcoholics who are known to have poor phagocytic cell activity.

BRIEF DESCRIPTION OF THE INVENTION

In order that the nature of the present invention may be more clearly understood preferred forms thereof will now be described with reference to the following examples and Figures in which.

Figure 1A:
FIG. 1a shows Arachidonic acid 5,8,11,14-Eicosatetraenoic acid
Figure 1B:
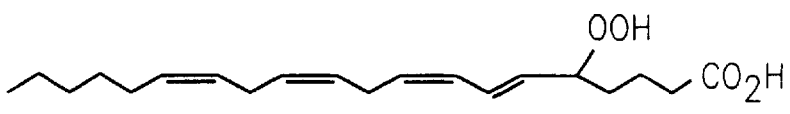
FIG. 1b shows 5-Hydroperoxy-6E,8Z,11Z,14Z-Eicosatetraenoic acid
Figure 1C:
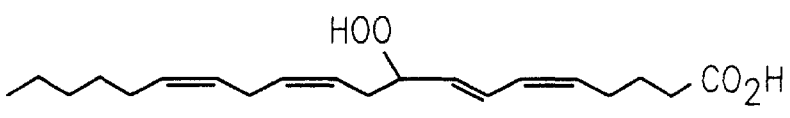
FIG. 1c shows 9-Hydroperoxy-5Z,7E,11Z,14Z-Eicosatetraenoic acid
Figure 1D:
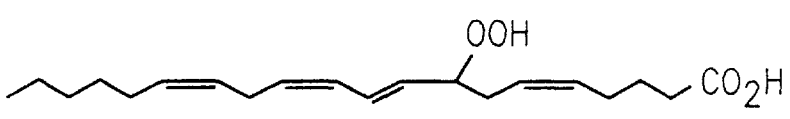
FIG. 1d shows 8-Hydroperoxy-5Z,9E,11Z,14Z-Eicosatetraenoic acid
Figure 1E:
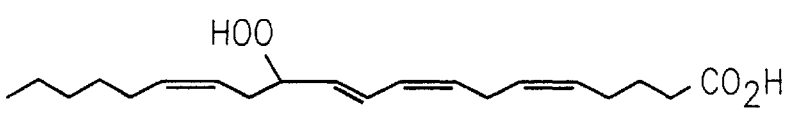
FIG. 1e shows 12-Hydroperoxy-5Z,8Z,10E,14Z Eicosatetraenoic acid
Figure 1F:
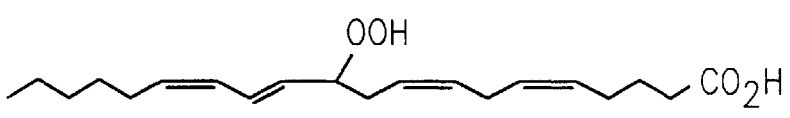
FIG. 1f shows 11-Hydroperoxy-5Z,8Z,12E,14Z Eicosatetraenoic acid
Figure 1G:
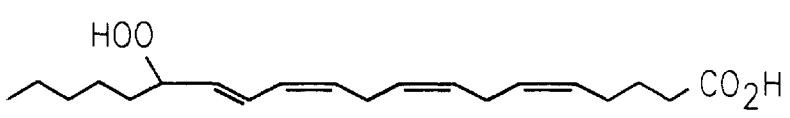
FIG. 1g shows 15-Hydroperoxy-5Z,8Z,11Z,13E Eicosatetraenoic acid
Figure 1H:
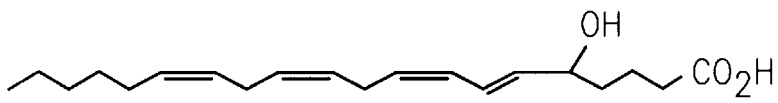
FIG. 1h shows 5-Hydroxy-6E,8Z,11Z,14Z-Eicosatetraenoic acid
Figure 1I:
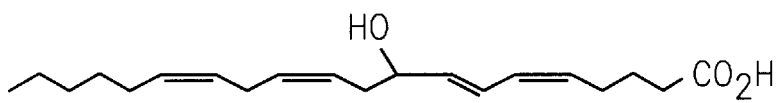
FIG. 1i shows 9-Hydroxy-5Z,7E,11Z,14Z-Eicosatetraenoic acid
Figure 1J:
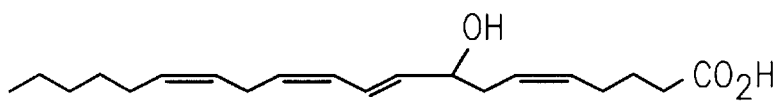
FIG. 1j shows 8-Hydroxy-5Z,9E,11Z,14Z-Eicosatetraenoic acid
Figure 1K:
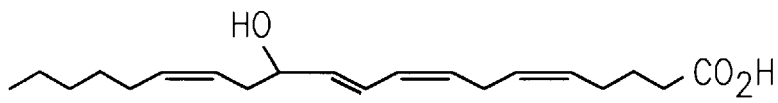
FIG. 1k shows 12-Hydroxy-5Z,8Z,10E,14Z Eicosatetraenoic acid
Figure 1L:
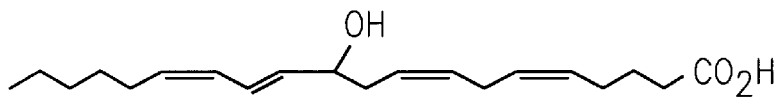
FIG. 1l shows 11-Hydroxy-5Z,8Z,12E,14Z Eicosatetraenoic acid
Figure 1M:
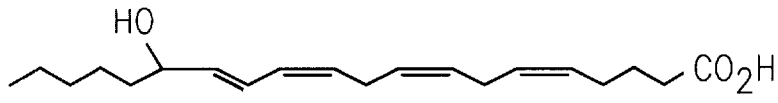
FIG. 1m shows 15-Hydroxy-5Z,8Z,11Z,13E Eicosatetraenoic acid

Table 1 shows the direct antimalarial activity of novel fatty acids against chloroquine sensitive *P. falciparum*.

Table 2 shows the ability of the novel fatty acids to stimulate neutrophils to kill *P. falciparum*.

Table 3 shows the direct effect of novel fatty acids on survival of chloroquine resistant *P. falciparum*.

Table 4 shows inhibition of mitogen stimulated proliferation of peripheral blood mononuclear proliferation by fatty acids.

Table 5 shows inhibition of PHA stimulated TNFα production by fatty acids.

Table 6 shows inhibition of *Staph aureus* stimulated interferony production by fatty acids.

METHODS

DETECTION OF TNF-INDUCED ELAM-1 AND ICAM-1

Human umbilical cord endothelial cells ($5\times10^{4}$ passage 1) were plated onto the centre 60 wells of 96 well microtrays, the remaining wells were filled with pyrongen-free distilled water to reduce evaporation in the wells containing cells. The cells were fed with fresh medium (M199 supplemented with 20% FCS and endothelial cell growth supplement) every second day until confluent. On the day preceding the assay the cells were washed with HBSS and re-fed. At the time of assay the medium was aspirated and fatty acides prepared in media were added to each well and incubated for various times as shown in FIGS. At 37-0-C in 5% $CO_2$. After this incubation the cells were washed and treated with either TNF or PMA before being washed three times in PBS and fixed (100 μl, 0.025% glutaraldehyde in PBS, overnight at 4° C.). The wells were washed with PBS and either anti-ELAM (Becton-Dickinson, 100 μl, 1/1.000 in M199 containing 20% FCS) or anti-ICAM (Immunotech, 100 μl, 12/2500 in M199 containing 20% FCS) was added and incubated for 1 hour at room temperature after which the wells were washed with PBS ant 100 μl of rabbit anti-mouse Ig-HRP conjugate was added (1/1.000. Dako). A further incubation at room temperature for one hour followed before the plates were washed three time prior to the addition of 100 μl of the substrate (ABTS). Colour development was measured at 410 nm in a microplate reader.

MONONUCLEAR CELL PROLIFERATION ASSAYS

Mononuclear cells were separated from peripheral blood of normal human donors as described by Ferrante and Thong (1978. . . ). The mononuclear cells were resuspended in RPMI-1640 containing 20% human AB serum and placed into 96 well microtrays (50 μl per well, cell density $4\times10^{0}$ cells/ml). Fatty acid (66 μm) was then added in 50 μl and pre-incubated with the cells for 30 min at 37° C. in 5% $CO_2$. Mitogen (PHA, ConA, PWM, Staph. aureus) was then added in 100 μl and the cells incubated for 66 hours at 37° C. in 5% $CO_2$ before the addition of tritiated thymidine (1 μCi/well). After a total of 72 h in culture the cells were harvested and proliferation (thymidine incorporation) and supernatant's assayed for the presence of cytokines.

CYTOKINE ASSAYS

Cytokine levels in culture supernatants were determined by specific ELISA using anti-cytokine antibodies. The following cytokine levels were determined TNFα, TNFβ, interferon-γ, IL-1β, IL-2.

PREPARATION OF FATTY ACID MICELLES AND PRETREATMENT OF NEUTROPHILS

To overcome fatty acid insolubility in aqueous solution mixed dipalmitoyl phophatidylcholine (DPC, 400 μg): fatty acid (100 μg) micells were prepared in HBSS by sonication. Neutrophils were pretreated for 30 min at 37° C. In some experiments PUFA were solubilized in ethanol.

MALARIA GROWTH INHIBITION ASSAY

Aliquots of RBC ($5\times10^{6}$ with 305% parasitaemia) was mixed with neutrophils ($10^{0}$) in the wells of a 96-well microtitre plate and than incubated for 2 hr at 37° C. in 5% $CO_2$ in air before adding 1 μCi of 3H-hypoxanthine. The plates were then incubated overnight. Individual well contents were collected onto glass filter paper and incorporated 3H measured in a liquid scintillation counter. Percent growth inhibition of the parasite was then calculated.

MEASUREMENT OF NEUTROPHIL CHEMILUMINESCENCE

To 100 μl of neutrophils ($1\times10^{6}$) in HBSS was added 100 μl of fatty acid micelles or DPC alone and an additional 300 μl of HBSS. This was followed immediately by the addition of 500 μl of lucigenin (0.25 mg/ml in PBS and the resulting light output ($m^V$) measured over time in a luminometer.

Experiments were performed in triplicate with cells from a separate individual and values presented represent peak values of the responses.

MEASUREMENT OF DEGRANULATION

Degranulation was determined by measuring vitamin B12 binding protein (as described by Gottleib et al., 1965, Blood 25:875–883) and β-glucuronidase release (as described by Kolodeney and Mumford, 1976, Clin. Chem. Acta 70:247–257).

BACTERICIDAL ASSAY

Neutrophil bactericidal activity against *Staphylococcus aureus* was measured according to the procedure described by Ferrante and Abell, 1986, Infect. Immun. 51:607.

CHEMICAL SYNTHESIS
Synthesis of β-Oxa Fatty Acids

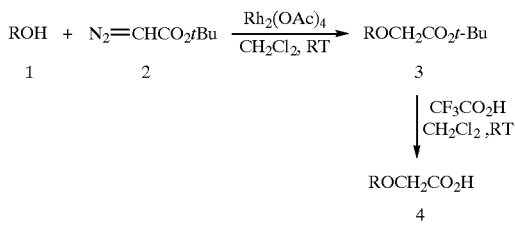

a: $R=CH_3(CH_2)_4(CH^{cis}=CHCH_2)_4(CH_2)_3$
b: $R=CH_3(CH_2)_4(CH^{cis}=CHCH_2)_3(CH_2)_4$
c: $R=CH_3CH_2(CH^{cis}=CHCH_2)_3(CH_2)_7$
d: $R=CH_3CH_2(CH^{cis}=CHCH_2)_6(CH_2)_2$
e: $R=CH_3CH_2(CH^{cis}=CHCH_2)_4(CH_2)_5$

REAGENTS

Arachidonyl Alcohol (1a) - Nu Chek Prep., Elysian, Minn. USA
Gamma Linolenyl Alcohol (1b) - Nu Chek Prep., Elysian, Minn. USA
Linolenyl Alcohol (1c) - Nu Chek Prep., Elysina, Minn. USA
Docosahexaenyl Alcohol (1d) - Nu Chek Prep., Elysian, Minn. USA
Z,Z,Z,Z-6, 9, 12, 15-Octadecatetraenyl alcohol (1e) - Synthesised by lithium aluminium hydride reduction of Methyl 6, 9, 12, 15-Octadecatetraenoate.
Methyl Z,Z,Z,Z-6, 9, 12, 15-Octadecatetraenoate - Sigma Chemical Company
Rhodium Acetate Dimer - Aldrich Chemical Company
tert-Butyl DiazoAcetate (2) - synthesized from tert-Butyl Acetoacetate as per: Regitz, M; Hocker, J; Leidhegener, A. *Organic Sytheses* Coll. Vol. 5, 179 tert-Butyl Acetoacetate - Fluka AG
Trifluoroacetic Acid - Aldrivch Chemical Company.
All solvents were distilled prior to use.
Column chromatographies were performed under positive nitrogen pressure on Merck Silica Gel 60 [230–400 mesh]. Art. 9385.

PROCEDURE
tert-Butyl alkyloxyacetates 3
The relevant fatty alcohol 1 (1 mol equivalent) was weighed into a two-neck round bottom flask under dry nitrogen and was dissolved in dichloromethane. To this stirred solution was added rhodium acetate dimer (0.5 mol %), followed by the dropwise addition of a solution of tert-butyl diazoacetate 2(2.5 mol equivalents) in dichloromethane via syringe. After the addition was complete the reaction mixture was stirred at room temperature under nitrogen for 2 hrs. The crude reaction mixture was concentrated under a stream of dry nitrogen and the residue was purified by column chromatography on silica, eluting with hexane/diethyl ether (9:1), to afford the relevant tert-butyl alkloxyecetate 3 as an oil.

ALKYLOXYACETIC ACIDS 4

The relevant tert-butyl alkyloxyacetate 3 (ca. 100 mg. 1 mol equivalent) was weighed into a two-neck round-bottom flask under dry nitrogen and was dissolved by the addition of dichloromethane (ca. 4 ml). To this stirred solution was added trifluoroacetic acid (ca. 1 ml), and the reaction mixture was stirred at room temperature under nitrogen for 2 hrs. The crude reaction mixture was concentrated under a stream of dry nitrogen and the residue was purified by column chromatography on silica, eluting with hexane/diethyl ether/acetic acid (40:60:2), to afford the relevant alkyloxyacetic acid 4 as an oil.

t-Butyl (5, 8, 11, 14-eicosatetraenyloxy) acetate (3a)
[t-Bu β-oxa 23:4 (n-6)]
$^1H$ n.m.r. (200 mnz. $CDCl_3$) δ 0.89 (3H, t.) 6.7 Hz. C20'—$H_3$, 1.25–1.38 (8H, m, C3'—$H_2$, C17'—$H_2$, C18'—$H_2$, C19'—$H_2$), 1.49 (9H, s, $C(CH_3)_3$), 1.56–1.69 (2H, m, C2'—$H_2$), 2.01–2.15 (4H, m, C4'—$H_2$, C16'—$H_2$), 2.79–2.87 (6H, m, C7'—$H_2$, C10'—$H_2$, C13'—$H_2$), 3.52 (2H, t, J6.6 Hz. C1'—$H_2$), 3.94 (2H, s, C2—$H_3$) 5.32–545 8H, m, C5'—H, C6'—H, C8'—H, C11'—H, C12'—H, C15'—H);
$^{13}C$ N,m,r, (50 MHz, $CDCl_3$) δ 169.82s, 130.48d, 129.97d, 128.55d, 128.42d, 128.08d, 128.02d, 127.96d, 127.59d, 81.40S, 71.63t, 68.83t, 31.58t, 29.29t, 29.07t, 28.14q, 27.23t, 27.01t, 26.09t, 25.66t, 22.57t, 14.09q.

t-Butyl Z,Z,Z-(6, 9, 12-octadecatrienyloxy) acetate (3b)
[t-Bu β-oxa 21:3)n-6)]
$^1H$ n.m.r. (200 MHz, $CDCl_3$) δ0.89 (3H, t, J 6.7 Hz, C18'—$H_3$, 1.25–1.45 (10H, m, C3'—$H_2$, C4'—$H_2$, C15'—$H_2$, C16'—$H_2$, C17'—$H_2$), 1.48 (9H, s, $C(CH_3)_3$), 1.56–1.68 (2H, m, C2'—$H_2$), 2.01–2.13 (4H, m, C5'—$H_2$, C14'—$H_2$), 2.77–2.84 ) 4H, m, C8'—$H_2$, C11'—$H_2$), 3.51 (2H, t, J6.6 Hz, C1'—$H_2$), 3.94 (2H, s, C2—$H_2$), 5.27–5.48 (6H, m, C6'—H, C7'—H, C9'—H, C10'—H, C12'—H, C13'—H);
$^{13}C$ n.m.r. (50 MHz, $CDCl_3$) δ 169.82s, 130.41d, 130.10d, 128.33d, 128.21d, 127.87d, 127.64d, 81.39s, 71.72t, 68.82t, 31.52t, 29.57t, 29.49t, 28.12q, 27.18t, 25.74t, 25.63t, 22.56t, 14.04q.

t-Butyl Z,Z,Z-(9, 12, 15-octadecatrienyloxy)acetate (3c)
[t-Bu β-oxa 21:3(n-3)]
$^1H$ n.m.r. (200 MHz, $CDCl_3$) δ 0.98 (3H, t, J 7.5 Hz, C18'—$H_3$), 1.25–1.40 (10H, m, C3'—$H_2$, C4'—$H_2$, C5'—$H_2$, C6'—$H_2$, C7'—$H_2$), 1.48 (9H, s, $C(CH_3)_3$), 1.51–1.67 (2H, m, C2'—$H_2$), 2.01–2.15 (4H, m, C8'—$H_2$, C17'—$H_2$), 2.75–2.86 (4H, m, C11'—$H_2$, C14'—$H_2$), 3.50 (2H, t, J6.6 Hz, C1'—$H_2$), 3.95 (2H, s, C2—$H_2$), 5.31–5.43 (6H, m, C9'—H, C10'—H, C12'—H, C13'—H, C15'—H, C16'—H);
$^{13}C$ n.m.r. (50 MHz, $CDCl_3$) δ 169.84s, 131.94d, 130.35d, 128.27d, 127.66d, 127.13d, 81.36s, 71.83t, 68.82t, 29.64t, 29.45t, 29.25t, 28.12q, 27.24t, 26.04t, 25.62t, 25.53t, 20.53t, 14.25q.

t-Buty Z,Z,Z,Z,Z,Z-(4,7,10,13,16,19-docosahexaenyloxy) acetate (3d)
[t-Bu B-oxa 25:6(n-3)
$^1H$ n.m.r. (200 MHz, $CDCl_3$) δ 0.98 (3H, t, J7.5 Hz, C22'—$H_3$), 1.48 (9H, s, $C(CH_3)_3$), 1.58–1.76 (2H, m, C2'—

H$_2$), 2.00–2.21 (4H, m, C3'—H$_2$, C21'—H$_2$), 2.79–2.87 (10H, m, C6'—H$_2$, C9'—H$_2$, C12'—H$_2$, C15'—H$_2$, C18'—H$_2$), 3.52 (2H, t, J 6.6 Hz, C1'—H$_2$), 3.95 (2H, s, C2—H$_2$), 5.28–5.46 (12H, m, C4'—H, C4'—H, C7'—H, C8'—H, C10'—H, C11'—H, C13'—H, C14'—H, C16'—H, C17'—H, C19'—H, C20'—H);

$^{13}$C n.m.r. (50 MHz, CDCL$_3$) δ 169.76s, 132.03d, 129.41d, 128.57d, 128.39d, 128.36d, 128.24d, 128.21d, 128.16d, 128.12d, 128.02d, 127.88d, 127.02d, 81.40s, 71.08t, 68.83t, 29.53t, 28.12q, 25.63t, 25.59t, 25.54t, 23.72t, 20.55t, 14.25q.

t/Butyl Z,Z,Z,Z-(6, 9, 12, 15-octadecatetraenyloxy acetate (3e)
[t/Bu β-oxa 21:4(n-3]

$^1$H n.m.r. (200 MHz, CDCl$_3$) δ 0.98 (3H, t, J 7.5 Hz, C18'—H$_3$), 1.21–1.52 (4H, m, C3'H$_2$), 1.48 (9H, s, C(CH$_3$)$_3$) 1.53–1.66 (2H, m, C2'—H$_2$.), 2.01–2.15 (4H, m, C5'—H$_2$, C17'—H$_2$), 2.77–2.87 (6H, m, C8'—H$_2$, C11'—H$_2$, C14'—H$_2$), 3.51 (3H, t, J6.6 Hz, C1'—H$_2$), 3.95 (2H, s, C2—H2), 5.28–5.47 (8H, m C6'—H, C7'H, C9'—H, C10'—H, C12'—H, C13'—H, C15'—H, C16'—H);

$^{13}$Cn.m.r. (50 MHz, CDCl$_3$) δ 169.82s, 132.00d, 130.15d, 128.49d, 128.42d, 128.01d, 127.96d, 127.78d, 127.05d, 81.39s, 71.71t, 68.81t, 29.57t, 29.49t, 28.12q, 27.18t, 25.74t, 25.63t, 25.54t, 20.55t, 14.25q.

Z,Z,Z,Z(5, 8, 11, 14-Eicosatetraenyloxy) acetic acid (4a)
[β-oxa 23:4(n-3)]

$^1$H n.m.r. (200 MHz, CDCl$_3$) δ 0.89 (3H, t, J 6.6 Hz, C20'—H$_3$), 1.25–1.490 (8H, m, C3'—H$_2$, C17,H$_2$, C18'—H$_2$, C19'—H$_2$), 1.57–1.74 (2H, m, C2'—H$_2$), 2.00–2.14 (4H, m, C4'—H$_2$, C16'—H$_2$), 2.78–2.85 (6H, m, C7'—H$_2$, C10'—H$_2$, C13'—H$_2$) 3.58 (2H, br t, J6.0 Hz, C1'—H$_2$), 4.08 (2H, s, C2—H$_2$), 5.29–5.46 (8H, m, C5'—H, C6'—H, C8'—H, C9'—H, C11'—H, C12'—H, C14'—H, C15'-H):

$^{13}$C n.m.r. (50MHz, CDCl$_3$) δ 173.37d, 130.47d, 129.64d, 128.55d, 128.24d, 128.13d, 128.02d, 127.86d, 127.152d, 71.81t, 31.49t, 29.49t, 29.21t, 27.20t, 26.88t, 26.03t, 25.63t, 2.63t, 22.54t, 14.02q.

Z,Z,Z-(6, 9, 12-Octadecatrienyloxy) acetic acid (4b)
[β-oxa 21:3(n-6)]

$^1$H n.m.r. (200 MHz, CDCl$_3$) δ 0.89 (3H, t, J 6.8 Hz, C18'—H$_3$), 1.23–1.43 (10H, m, C3'—H2, C4'—H2, C15'—H2, C16'—H2, C17'—H2)), 1.51–1.71 (2H, m, C2'—H2), 2.00–2.10 (4H, m, C4'—H2, C14'—H2), 2.75–2.86 (4H, m, C8'—H2, C11'—H2), 3.60 (2H, t, J 6.6 Hz, C1'—H2) 4.17 (2H, s, C2—H2), 5.26–5.47 (6H, m, C6'—H, C7'—H, C9'—H, C10'—H, C12'—H, C13'—H)

$^{13}$C n.m.r. (50 MHz, CDCl$_3$) δ 171.74s, 130.45d, 129.84d, 128.40d, 128.20d, 128.10d, 127.59d, 71.13d, 31.51d, 29.36d, 29.31d, 27.20d, 27.10d, 25.62d, 22.57d, 22.55d, 14.04q.

Z,Z,Z-(9, 12, 15-Octadecatrienyloxy) acetic acid (4c)
[β-oxa 21:3(n-3)]

$^1$H n.m.r. (200 MHz, CDCl$_3$) δ 0.97 (3H, t, J 7.5 Hz, C18'—H$_3$), 1.25–1.43 (10H, m, C3'—H$_2$, C4'—H$_2$, C5'—H$_2$, C6'—H$_2$, C7'—H$_2$), 1.51–1.63 (2H, m, C2'—H$_2$), 2.01–2.15 (4H, m, C8'—H$_2$, C17'—H$_2$), 2.75–2.86 (4H, m, C11'—H$_2$, C14'—H$_2$), 3.55 (2H, t, J 6.5 Hz, C1'—H$_2$), 4.12 (2H, s, C2'—H$_2$), 5.28–5.46 (6H, m, C9'—H, C10'—H, C12'—H, C13'—H, C15'—H, C16'—H):

$^{13}$C n.m.r. (50 MHz, CDCL$_3$) δ 174.73s, 131.93d, 130.29d, 128.25d, 127.68d, 127.11d, 72.16t, 29.60t, 29.41t, 29.20t, 27.21t, 25.88t, 25.60t, 25.52t, 20.53t, 14.24q.

Z,Z,Z,Z,Z,Z-(4, 7, 10, 13, 16, 19-Docosahexaenyloxy) acetic acid (4d)
[β-oxa 25:6(n-3)]

$^1$H n.m.r. (200 MHz, CDCl$_3$) δ 0.97 (3H, t, J 7.5 Hz, C22'—H$_3$), 1.65–1.78 (2H, m, C2'—H$_2$), 2.01–2.21 (4H, m, C3'—H$_2$, C21'—H$_2$), 2.75–2.92 (10H, m, C6'—H$_2$, C9'—H$_2$, C12'—H$_2$, C15'—H$_2$, C18'—H$_2$), 3.57 (2H, t, J 6.4 Hz, C1'—H$_2$), 4.12 (2H, s, C2—H$_2$), 5.28–5.46 (12H, m, C4'—H, C5'—H, C7'—H, C8'—H, C10'—H, C11'—H, C13'—H, C14'—H, C16'—H, C17'—H, C19'—H, C20'H), 10.22 (1H, br, CO$_2$H)

—C n.m.r. (50 MHz, CDCl$_3$) δ 172.99s, 132.04d, 128.98d, 128.75d, 128.59d, 128.49d, 128.38d, 128.28d, 128.22d, 128.17d, 128.08d, 127.86d, 127.01d, 71.48t, 29.26t, 25.64t, 25.59t, 25.54t, 23.55t, 14.25q.

Z,Z,Z,Z-(6, 9, 12, 15-Octadecatetraenyloxy) acetic acid (4e)
[β-oxa 21:4(n-3)]

$^1$H n.m.r. (200 Mhz, CDCl$_3$) δ 0.97 (3H, t, J 7.5 Hz, C18'—H$_3$), 1.33–1.40 (4H, m, C3'—H$_2$, C4'—H$_2$), 1.54–1.68 (2H, m, C2'—H$_2$), 2.00–2.15 (4H, m, C5'—H$_2$, C17'—H$_2$), 2.77–2.87 (6H, m, C8'—H$_2$, C11'—H$_2$, C14'—H$_2$), 3.56 (3H, t, J 6.6 Hz, C1'—H$_2$), 4.11 (2H, s, C2–H2), 5.24–5.45 (8H, m, C6'—H, C7'—H, C9'—H, C10'—H, C12'—H, C13'—H, C15'—H, C16'—H):

$^{13}$C n.m.r. (50 MHz, CDCl$_3$) δ 172.05s, 132.03d, 139.92d, 128.53d, 128.35d, 128.08d, 128.01d, 127.94d, 127.04d, 71.10t, 29.34t, 27.10t, 25.64t, 25.55t, 20.55t, 14.25q.

Synthesis of β and γ Thia fatty acids.

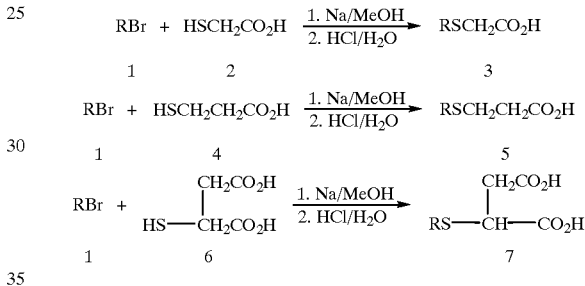

a: R=CH$_3$(CH$_2$)$_4$(CH$^{cis}$=CHCH$_2$)$_4$(CH$_2$)$_3$
b: R=CH$_3$(CH$_2$)$_4$(CH$^{cis}$=CHCH$_2$)$_3$(CH$_2$)$_4$
c: R=CH$_3$CH$_2$(CH$^{cis}$=CHCH$_2$)$_3$(CH$_2$)$_7$
d: R=CH$_3$CH$_2$(CH$^{cis}$=CHCH$_2$)$_0$(CH$_2$)$_2$ Reagents Fatty bromides (1a-1d)—synthesized from the corresponding fatty alchohols by treatment with triphenylphosphine and carbon tetrabromide in dichloromethane.

Arachidonyl alchohol - Nu Chek Prep.
Gamma linolenyl alchohol - Nu Chek Prep
Linolenyl alchohol - Nu Check Preo
Docosahexaenyl alchohol - Nu Check Prep
Mercaptoacetic acid - Aldrich Chemical Company
Mercaptoproprionic acid - Aldrich Chemical Company
All solvents were distilled prior to use.
Column chromatographies were performed under positive nitrogen pressure on Merck Silica Gel 60 (230–400 mesh), Art. 9385.

PROCEDURE

Alkylthioacetic acids 3a–d

Sodium (3mol equivalents) was dissolved in methanol in a two-neck round-bottomed flask under dry nitrogen and to this stirred solution was added mercaptoacetic acid (1.2 mol equivalents). After the initial white precipitate had dissolved, a solution of the relevant bromide 1 (1 mol equivalent) in diethyl ether was added via syringe and the mixture was stirred at room temperature under nitrogen for 16 hr. The crude reaction mixture was poured into an equal volume of hydrochloric acid (10% v/v) and extracted with diethyl ether. The resulting extract was concentrated under a stream of dry nitrogen and the residue was purified by flash chromatography on silica, eluting with hexane/diethyl ether/acetic acid (40:60:2) to afford the relevant alkylthioacetic acid 3 as an oil.

Alkylthioprionic acids 5a–c

The alkylthioprionic acids 5a–c were synthesized by alkaline condensation of the respective fatty bromides 1a–c with mercaptoproprionic acid 4, in an analogous manner to that described above for the alkylthioacetic acids 3a–d.

Z,Z,Z,Z-(5,8,11,14-Eicosatetraenylthio)succinic Acid 7a (5,8,11,14-Eicosatetraenylthio)succinic acid 7a was synthesized by condensation of the fatty bromide 1a (1 mol equivalent) with mercaptosuccinic acid 6 (1.2 mol equivalents), in the presence of sodium (4.5 mol equivalents) in an analogous manner to that described above for the alkylthioacetic acids 3a–d.

Z,Z,Z,Z-(5,8,11,14-Eicosatetraenylthio) acetic acid (3a) [β-thia 23:4 (n-6)]

$^1$H n.m.r. (200 MHz, CDCl$_3$) δ 0.89 (3H, t, J 6.7 Hz, C20'—H$_3$), 1.21–1.54 (8H, m, C3'—H$_2$, C17'—H$_2$, C18'—H$_2$, C19'—H$_2$), 157–1.72 (2H, m, C2'—H$_2$), 2.01–2.14 (4H, m, C4'—H$_2$, C16'—H$_2$), 2.67 (2H, t, J 7.2 Hz, C2'—H$_2$), 2.73–2.88 (6H, m, C7'—H$_2$ C10'—H$_2$, C13'—H$_2$), 3.25 (2H, s, C2–H$_2$), 5.27–5.47 (8H, m, C5'—H, C6'—H, C8'—H, C9'—H, C11'—H, C12'—H, C14'—H, C15'—H);

$^{13}$C n.m.r. (50 MHz, CDCl$_3$) δ 175.69s, 130.49d, 129.54d, 128.56d, 128.27d, 128.15d, 127.89d, 127.55d, 33.45t, 32.70t, 31.51t, 30.38t, 29.32t, 28.62t, 28.46t, 27.23t, 26.73t, 25.65t, 22.57t, 14.05q.

Z,Z,Z,Z-(6,9,12-Octadecatrienylthio)acetic acid (3b) [β-thia 21:3(n-6)]

$^1$H n.m.r. (200 MHz, CDCl$_3$) δ 0.89 (3H, t, J 6.6 Hz, C18'—H$_3$), 1.23–1.48 (10H, m, C3'—H$_2$, C4'—H$_2$C15'—H$_2$, C18'—H$_2$, C17'—H$_2$), 1.52–1.70 (2H, m, C2'—H$_2$), 1.89–2.15 (4H, m, C5'—H$_2$, C14'—H$_2$), 2.63 (2H, t, J 7.0 Hz. C1'—H$_{21}$), 2.70–2.87 (4H, m, C8'—H$_2$C11'—H$_2$), 3.26 (2H, s, C2–H$_2$), 5.29–5.47 (6H, m, C6'—H, C7'—H, C9'—H, C10'—H, C12'—H, C13'—H):

$^{13}$C n.m.r. (50 MHz, CDCl$_3$) δ 176.54s 130.41d, 129.86d, 128.367d, 128.11d, 128.03d, 128.59d, 33.49t, 32.74t, 31.51t, 30.36t, 29.31t, 29.14t, 28.81t, 28.34t, 27.21t, 27.05t, 25.63t, 22.55t, 14.04q.

Z,Z,Z-(9,12,15-Octadecatrienylthio)acetic acid (3c) [β-thia 21:3(n-3)]

$^1$H n.m.r. (200 MHz, CDCl$_3$) δ 0.89 (3H, t, J 6.7 Hz, C18'—H$_3$), 1.21–1.52 (10H, m, C3'—H$_2$, C4'—H$_2$, C5'—H$_2$, C6'—H$_2$, C7'—H$_2$), 1.54–1.72 (2H, m, C2'—H$_2$), 2.01–2.15 (4H, m, C8'—H$_2$, C17'—H$_2$), 2.67 (2H, t, J 7.2 Hz, C1'—H$_{21}$), 2.73–2.87 (4H, m, C11'—H$_2$, C14'—H$_2$), 3.25 (2H, s, C2–H$_2$), 5.27–5.48 (6H, m, C9'—H, C10'—H, C12'—H, C13'—H, C15'—H, C16'—H)

$^{13}$C n.m.r. (50 MHz, CDCl$_3$) δ 176.21s, 131.94d, 130.29d, 128.26d, 127.69d, 127.11d, 33.49t, 32.82t, 30.39t, 29.60t, 29.36t, 29.20t, 29.12t, 28.89t, 28.70t, 27.21t, 25.61t, 25.52t, 20.53t, 14.25q.

Z,Z,Z,Z,Z,Z-(9,12,15-Octadecatrienylthio)acetic acid (3d) [β-thia 25:6(n-3)]

$^1$H n.m.r. (200 MHz, CDCl$_3$) δ 0.99 (3H, t, J 7.5 Hz, C22'—H$_3$), 1.62–1.77 (2H, m, C2'—H$_2$,), 2.02–2.24 (4H, m, C3'—H$_2$, C21'—H$_2$), 2.68 (2H, t, J 7.4 Hz, C1'—H$_2$), 2.83–2.85 (10H, m., C6'—H$_2$, C9'—H$_2$, C12'—H$_2$, C15'—H$_2$, C18'—H$_2$), 3.26 (2H, s, C2–H$_2$), 5.29–5.47 (12H, m, C4'—H, C5'—H, C7'—H, C8'—H, C10'—H, C11'—H, C13'—H, C14'—H, C16'—H, C17'—H, C19'—H, C20'—H);

$^{13}$C n.m.r. (50 MHz, CDCl$_3$) δ 176.37s, 132.01d, 128.94d, 128.68d, 128.55d, 128.24d, 128.18d, 128.12d, 128.07d, 127.85d, 126.99d, 33.41t, 32.21t, 28.67t, 26.12t, 25.64t, 25.22t, 20.53t, 14.24q.

Z,Z,Z,Z-(5,8,11,14-Eicosatetraenylthio) propionic acid (5a) [γ-thia 24:4(n-6)]

$^1$H n.m.r. (300 MHz, CDCl$_3$) δ 0.89 (3H, t, J 6.8 Hz. C20'—H$_3$), 1.26–1.38 (6H, m, C17'—H$_2$, C18'—H$_2$, C19'—H$_2$), 1.41–1.51 (2H, m, C3'—H$_2$), 1.56–1.66 (2H, m, C2'—H$_2$), 2.02–2.12 (4H, m, C4'—H$_2$, C16'—H$_2$), 2.54 (2H, t, J 7.3 Hz. C1'—H$_3$), 2.66 (2H, t, J 6.6 Hz C3–H$_2$), 2.78 (2H, t, J 6.6 Hz, C2–H$_2$), 2.78–2.86 (6H, m, C7'—H$_2$, C10'—H$_2$, C13'—H$_2$), 5.29–5.44 (8H, m, C5'—H, C6'—H, C8'—H, C9'—H, C11'—H, C12'—H, C14'—H, C15'—H):

$^{13}$C n.m.r. (50 MHz, CDCl$_3$) δ 178.22s, 130.37d, 129.58d, 128.46d, 128.19d, 128.10d, 128.03d, 127.81d, 127.48d, 34.68t, 32.046t, 31.44t, 29.25t, 29.01t, 28.67t, 27.15t, 26.70t, 26.54t, 25.57t, 22.50t, 13.98q.

Z,Z,Z-(6,9,12-Octadecatrienylthio)propionic acid (5b) [γ-thia 22:3(n-6)]

$^1$H n.m.r. (200 MHz, CDCl$_3$) δ 0.89 (3H, t, J 6.8 Hz, C18'—H$_3$), 1.25–1.42 (10H, m, C3'—H$_2$, C4'—H$_2$, C15'—H$_2$, C16'—H$_2$, C17'—H$_2$), 1.53–1.85 (2H, m, C2'—H$_2$), 2.01–2.10 (4H, m, C5'—H$_2$, C14'—H$_2$), 2.53 (2H, t, J 7.3 Hz, C1'—H$_2$), 2.66 (2H, t, J 6.8 Hz, C3—H$_2$), 2.78 (2H, t, J 6.8 Hz C2 —H$_2$), 2.74–2.83 (4H, m, C8'—H, C11'—H) 5.26–5.47 (6H, m, C6'—H, C7'—H, C9'—H, C10'—H, C12–H, C13–H);

$^{13}$C n.m.r. (50 MHz, CDCl$_3$) δ 178.14s, 130.38d, 129.90d, 128.33d, 128.10d, 127.97d, 127.58D, 34.69t, 32.13t, 31.49t, 29.41t, 29.29t, 29.18t, 28.46t, 27.19t, 27.06t, 26.58t, 25.61t, 14.03q.

Z,Z,Z-(9,12,15-Octadecatrienylthio)proponionic acid (5c) [γ-thia 22:3(n-3)]

$^1$H n.m.r. (200 MHz, CDCl$_3$) δ 0.98 (3H, t, J 7.5 Hz, C18'—H$_3$), 1.26–1.35 (10H, m, C3'—H$_2$, C4'—H$_2$, C5'—H$_2$, C6'—H$_2$, C7'—H$_2$), 1.51–1.65 (2H, m, C2'—H$_2$), 1.98–2.15 (4H, m. C8'—H$_2$, C17'—H$_2$), 2.53 (2H, t, J 7.3 Hz, C1'—H$_2$), 2.66 (2H, t, J 6.7 Hz, C3'—H$_2$), 2.78 (2H, t, J 7.3 Hz, C1'—H$_2$), 2.66 (2H, t, J 6.7 Hz, C3'—H$_2$), 2.78 (2H, t, J 6.7 Hz, C2'—H$_2$), 2.75–2.84 (4H, m, C11'—H$_2$, C14'—H$_2$) 5.27=5.46 (6H, m, C9'—H, C10'—H, C12'—H, C15–H, C16'—H);

$^{13}$C n.m.r. (50 MHz, CDCl$_3$) δ 178.03s, 131.92d, 130.28d, 128.24d, 127.66d, 127.10d, 34.67t, 32.19t, 29.58t, 29.50t, 29.37t, 29.20t, 29.16t, 28.81t, 27.19t, 26.59t, 25.59t, 25.50t, 20.52t, 14.245q.

Z,Z,Z,Z-(5,8,11,14-Octadecatrienylthio)succinic acid (7a) [α-carboxymethyl-β-thia 23:4(n-6)]

$^1$H n.m.r. (300 MHz, CDCl$_3$) δ 0.89 (3H, t, J 6.8Hz, C20'—H$_3$), 1.23–1.53 (8H, m, C3'—H$_2$, C17'—H$_2$, C18'—H$_2$, C19'—H$_2$), 1.56–1.70 (2H, m, C2'—H$_2$), 2.03–2.13 (4H, m, C4'—H$_2$, C16'—H$_2$), 2.65–2.86 (9H, m, C7'—H$_2$, C10'—H$_2$, C13'—H$_2$, C1'—H$_2$, CHHCO$_2$H), 3.01 (1H, dd, J 12.1, 17.6 Hz,CHHCO$_2$H), 3.64 (1H, dd, J 4.0, 12.1 Hz,C2–H), 5.32–5.43 (8H, m, C5'—H, C6'—H, C8'—H, C9'—H, C11'—H, C12'—H, C14'—H, C15'—H);

SYNTHESIS OF HYDROXY AND HYDROPEROXY DERIVATIVES

The hydroperoxide derivatives of arachidonic acid (FIGS. 1b–1g) are obtained separately from enzyme-catalysed reactions of FIG. 1a, or as a mixture by autoxidation of FIG. 1a. The components of the autoxidation mixture FIGS. 1b–1g, which vary in ratio depending on the reaction conditions, can be separated by high performance liquid chromatography on silica. Reduction of the hydroperoxides FIGS.

Figure 1N:
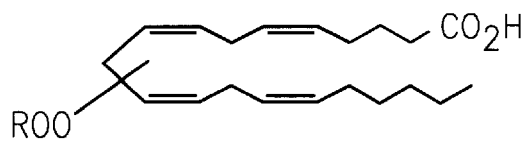
FIG. 1n to FIG. 1z show a range of substituted PUFAs in which Y is hydroxy. hydroperoxy or peroxy.
Figure 1O:
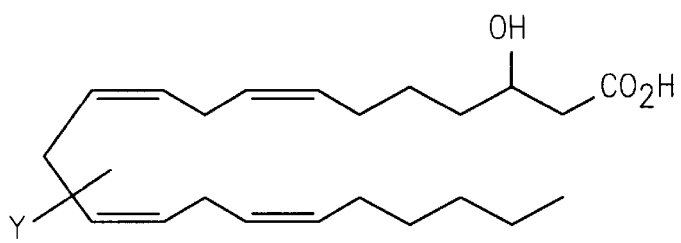
Figure 1P:
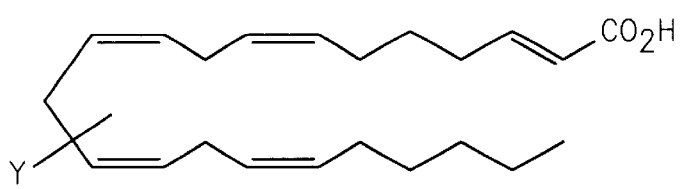
Figure 1Q:
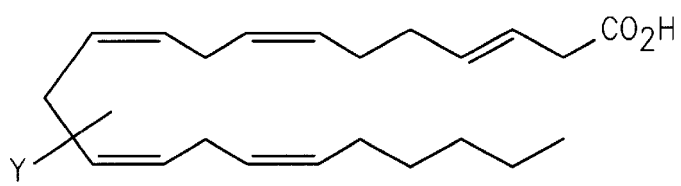
Figure 1R:
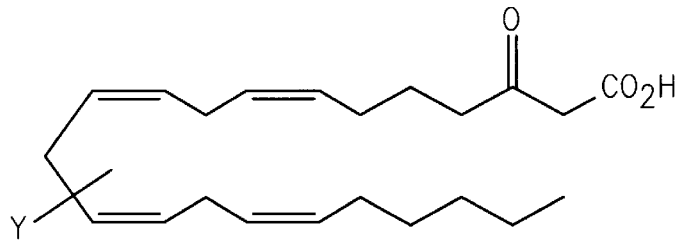
Figure 1S:
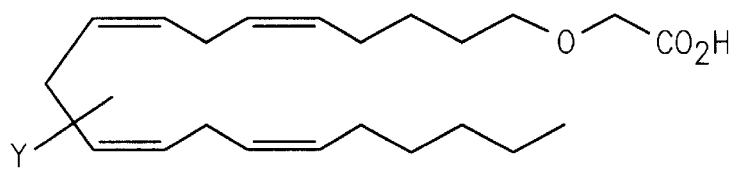
Figure 1T:
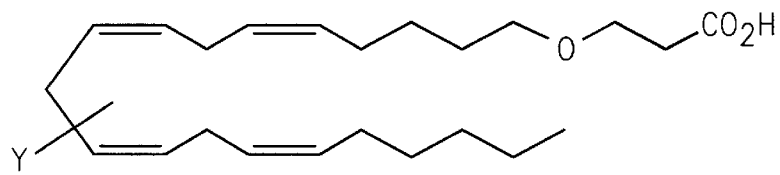
Figure 1U:
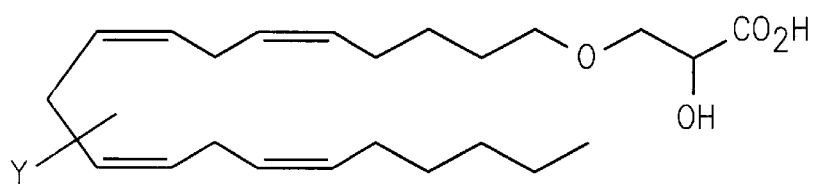
Figure 1V:
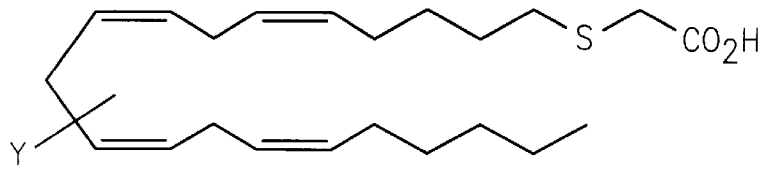
Figure 1W:
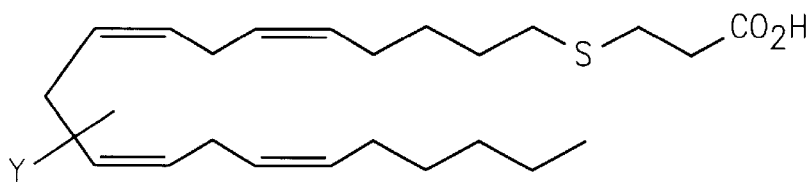
Figure 1X:
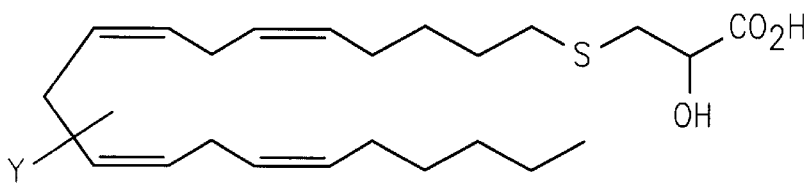

1b–1g, either separately or as a mixture affords the corresponding alchohols FIGS. 1h–1m. These can be converted to the corresponding peroxides FIG. 1n (R-alkyl or aryl), having the same substitution pattern as the hydroperoxides FIGS. 1b–1g and alcohols FIGS. 1h–1m, by treating with a variety of reagents including the corresponding alkyl or aryl hypohalites (ROX). Mixtures of either the alchols FIGS. 1h–1m or the peroxides FIG. 1n can also be separated by high performance liquid chromatography.

Figure 1Y:
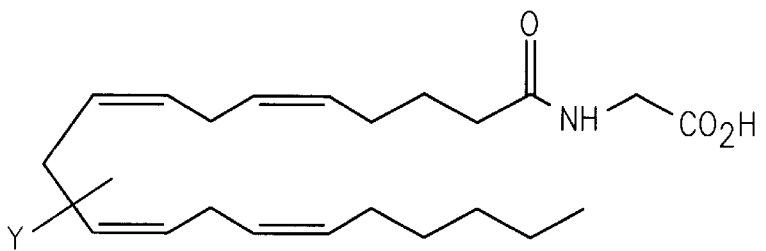
Figure 1Z:
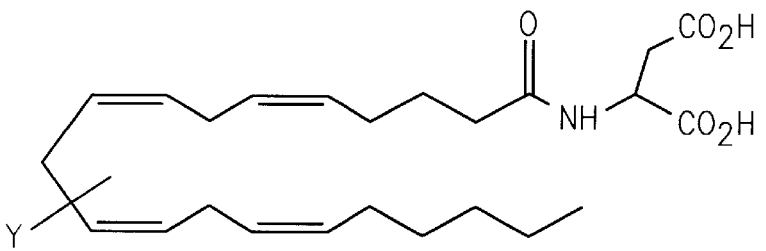
Figure 2A:
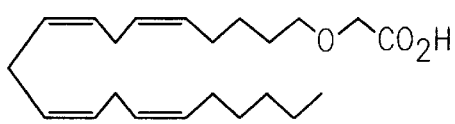
FIG. 2a shows β-oxa 23:4 (n-6)
Figure 2B:
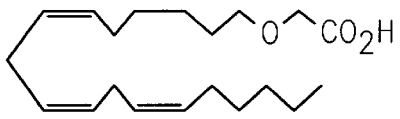
FIG. 2b shows β-oxa 21:3 (n-6)
Figure 2C:
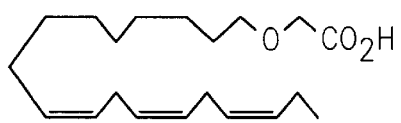
FIG. 2c shows β-oxa 21:3 (n-3)
Figure 2D:
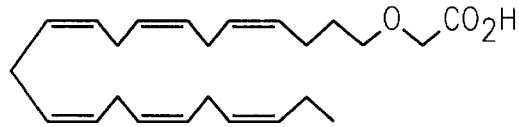
FIG. 2d shows β-oxa 25:6 (n-3)
Figure 2E:
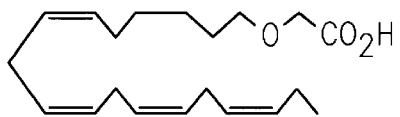
FIG. 2e shows β-oxa 21:4 (n-3)
Figure 2F:
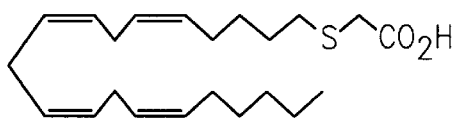
FIG. 2f shows β-thia 23:4 (n-6)
Figure 2G:
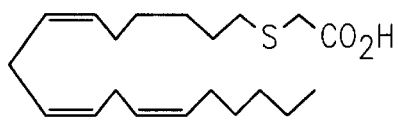
FIG. 2g shows β-thia 21:3 (n-6)
Figure 2H:
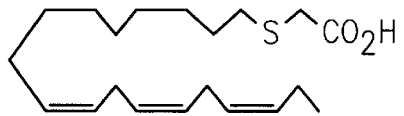
FIG. 2h shows β-thia 21:3 (n-3)
Figure 2I:
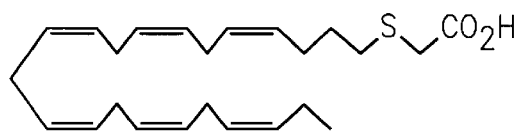
FIG. 2i shows β-thia 25:6 (n-3)
Figure 2J:
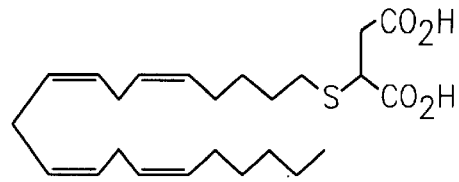
FIG. 2j shows α-carboxymethyl-β-thia 23:4 (n-6)
Figure 2K:
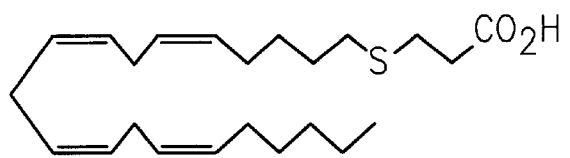
FIG. 2k shows γ-thia 24:4 (n-6)
Figure 2L:
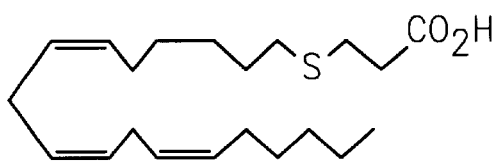
FIG. 2l shows γ-thia 22:3 (n-6)
Figure 2M:
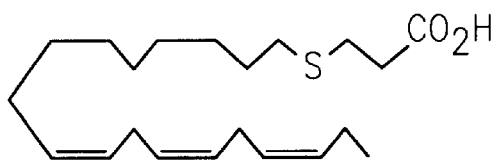
FIG. 2m shows γ-thia 22:3 (n-3)
Figure 2N:
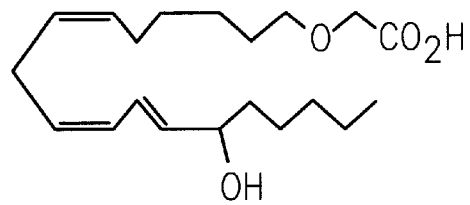
FIG. 2n shows 16-OH-β-oxa 22:3 (n-6)
Figure 2O:
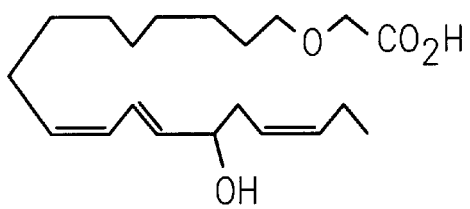
FIG. 2o shows 16-OH-β-oxa 22:3 (n-3).
Figure 3:
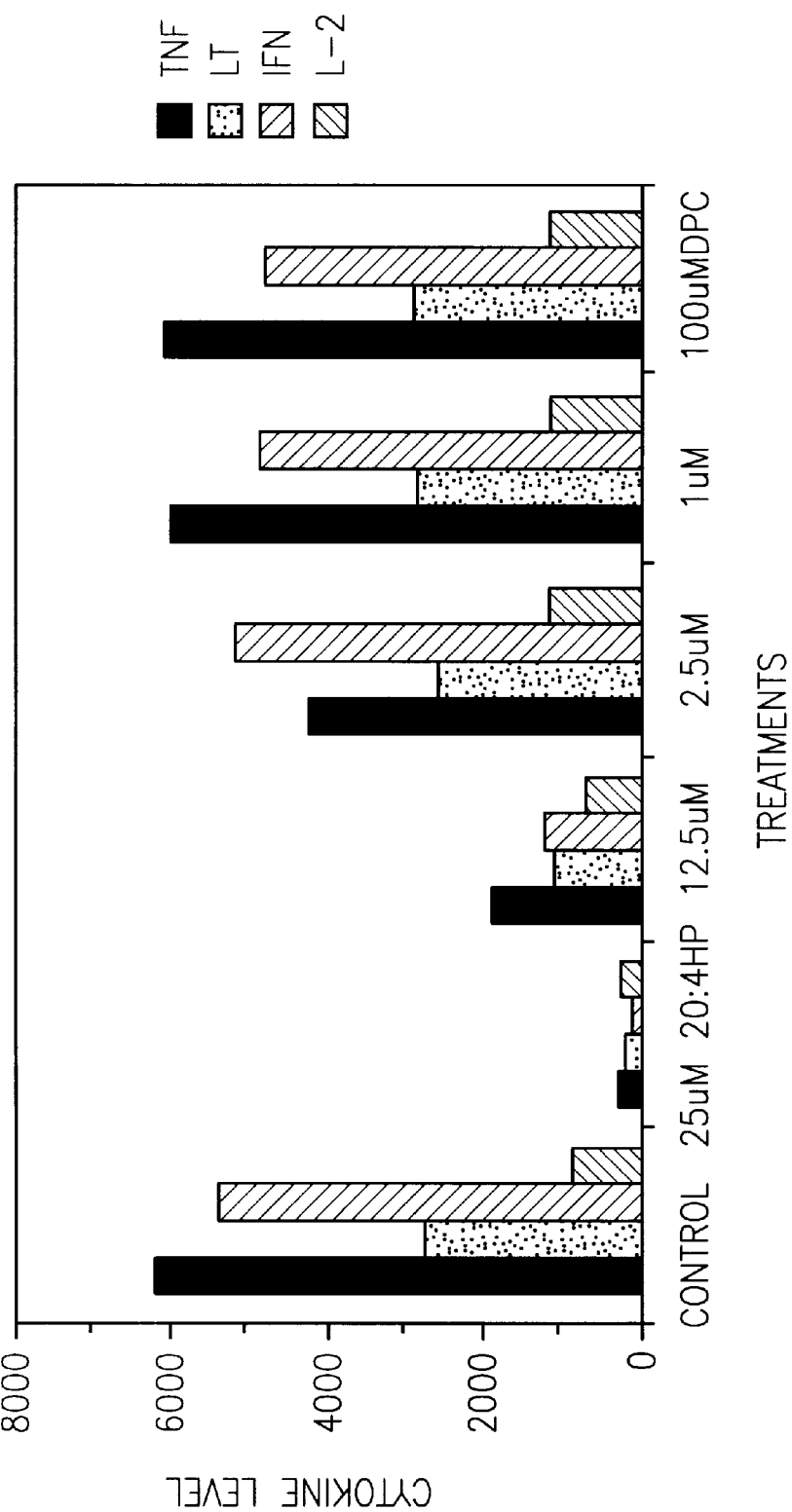
FIG. 3 shows the effect of 20:4, 20:4 methyl ester (ME), 20:4 hydroperoxy (HP) and 20:4 hydroxy (H) on cytokine production by human peripheral blood mononuclear cells (PBMC) stimulated by the mitogen PHA. 20:4 hydroperoxy and 20:4 hydroxy inhibit cytokine production, both macrophage-derived cytokines (TNFα) and T cell derived cytokines (lymphokines, interferon, IL-2).
Figure 4:
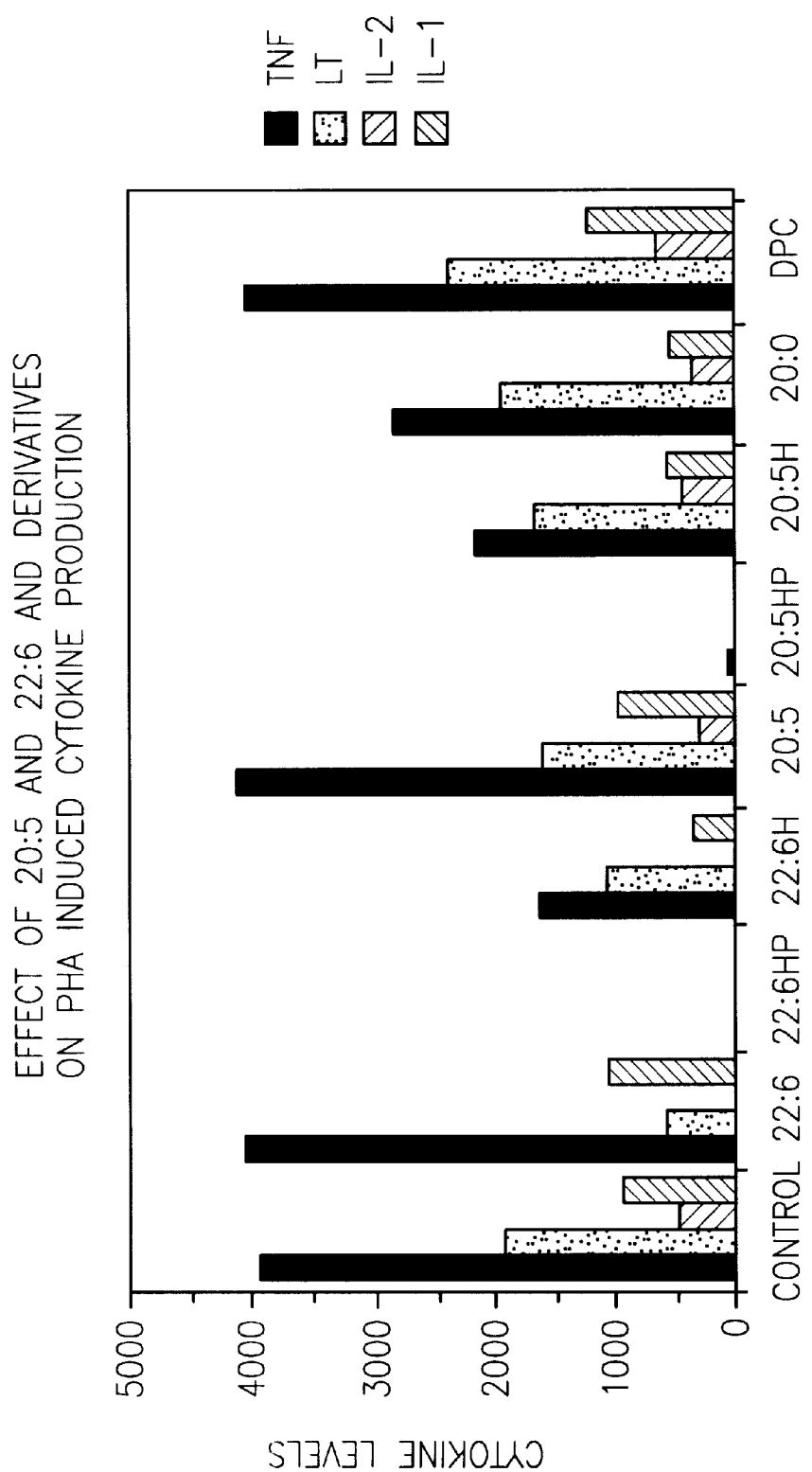
FIG. 4 shows the effect of 22:6, 22:6HP, 22:6H, 20:5, 20:5HP and 20:5H on PHA-induced cytokine production. These compounds inhibit in vitro production of macrophage and T cell-derived cytokines.
Figure 5:
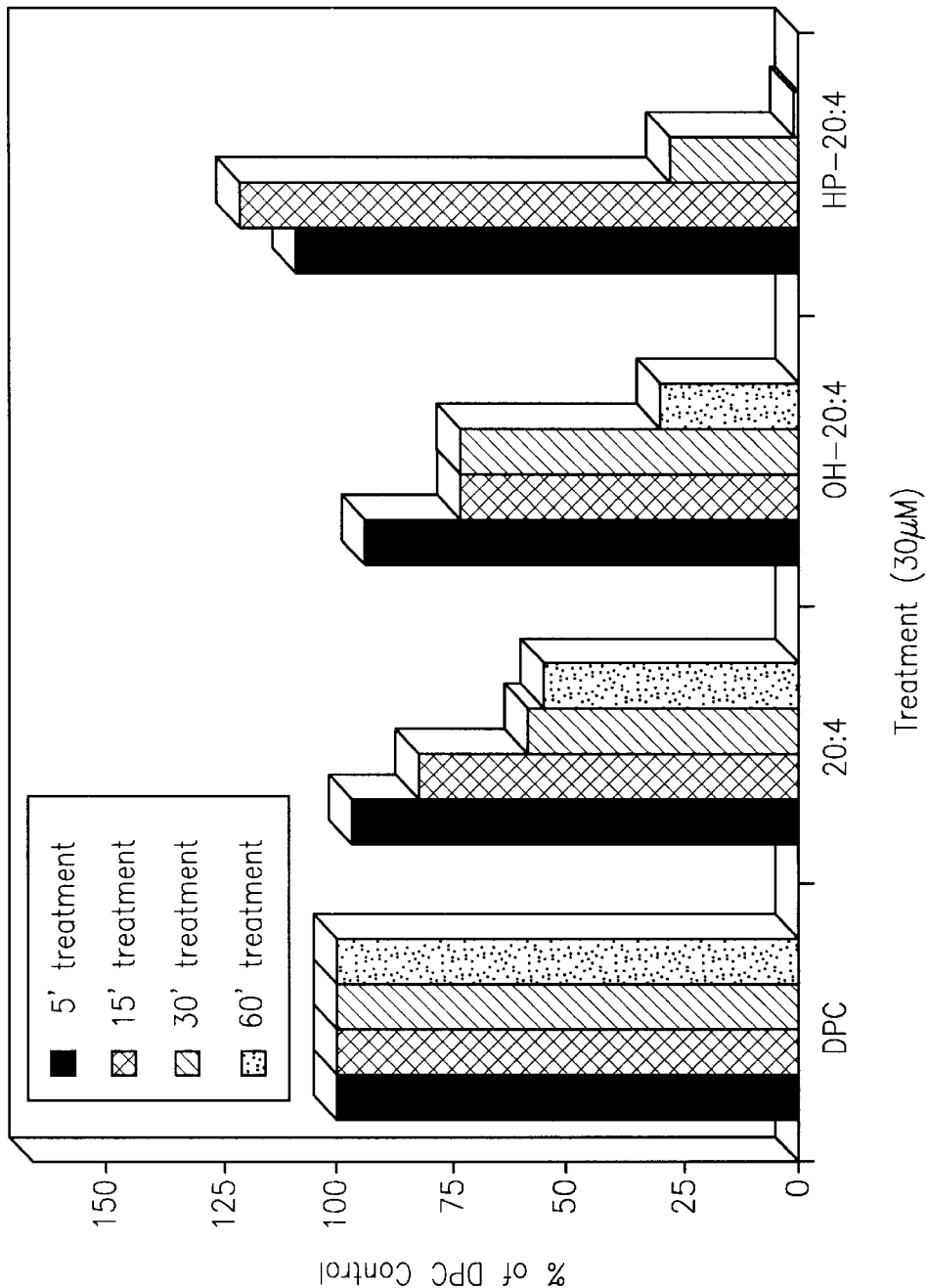
FIG. 5 shows 20:4, 20:4 hydroperoxy (HP) and 20:4 hydroxy (OH) inhibit TNFα-induced expression of E-selection by human umbilical vein endothelial cells.
Figure 6:
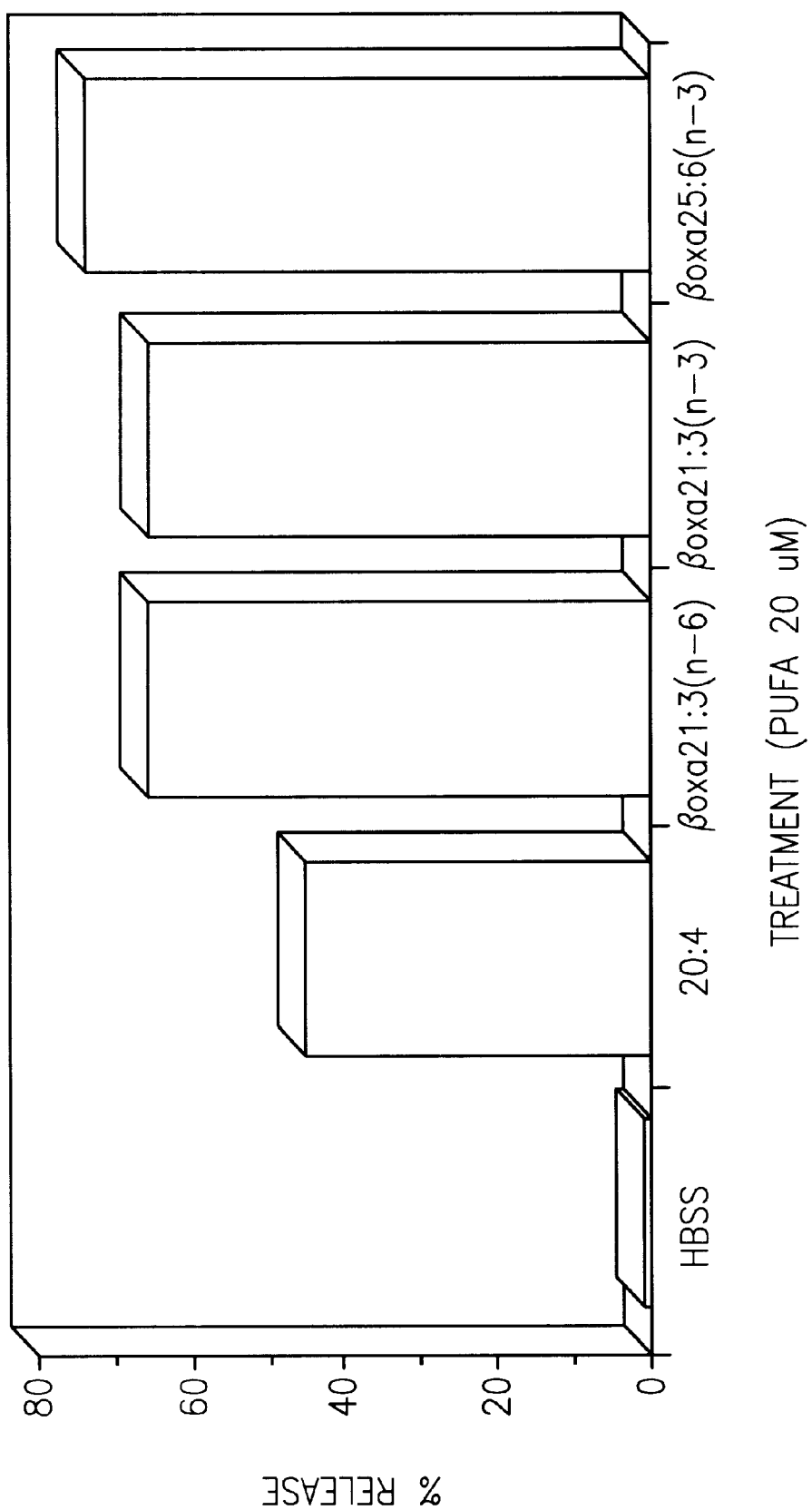
FIG. 6 shows the fatty acid stimulated release from neutrophil azurophilic granules.
Figure 7:
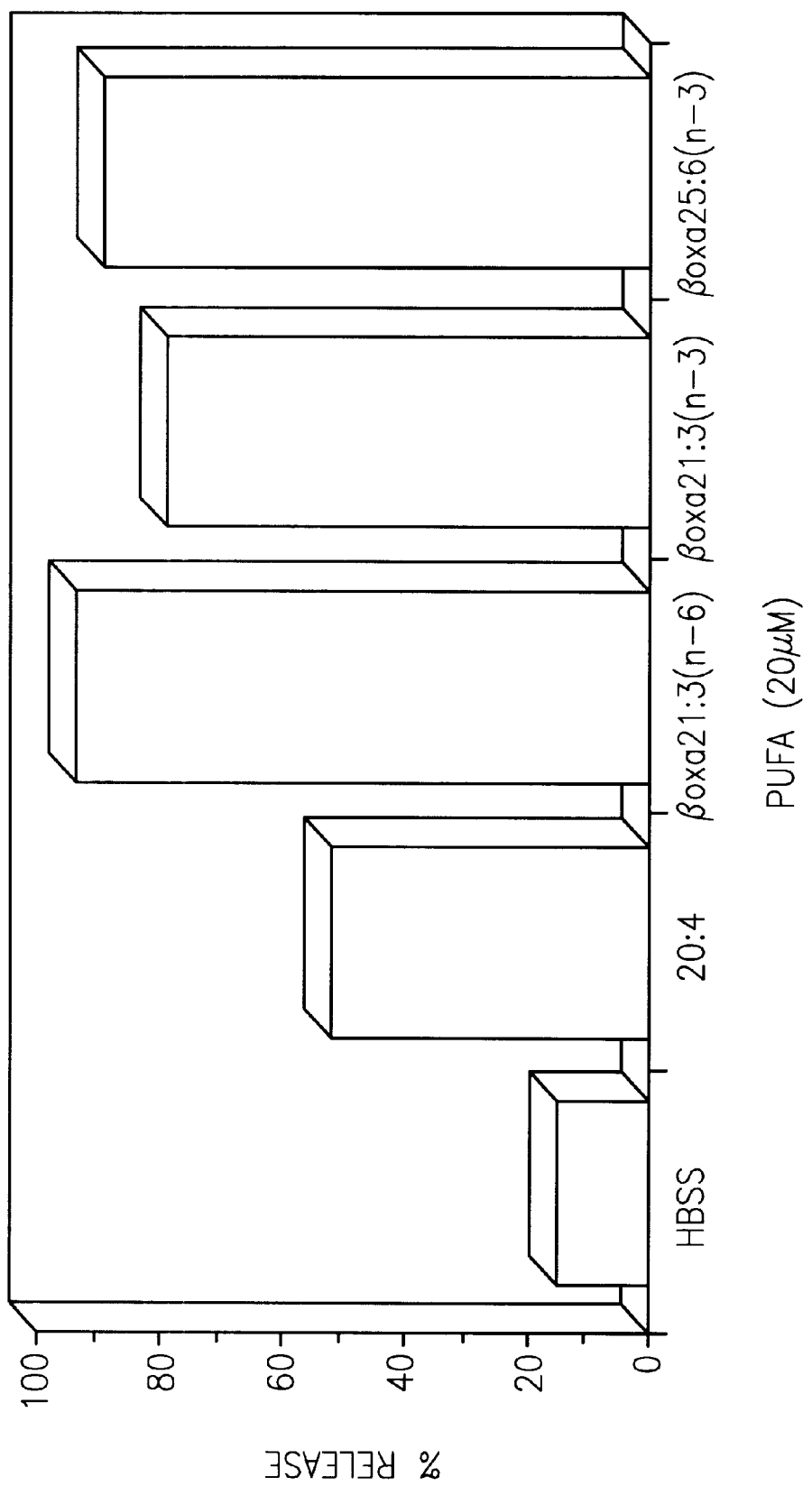
FIG. 7 shows the fatty acid stimulated release from neutrophil specific granules.
Figure 8:
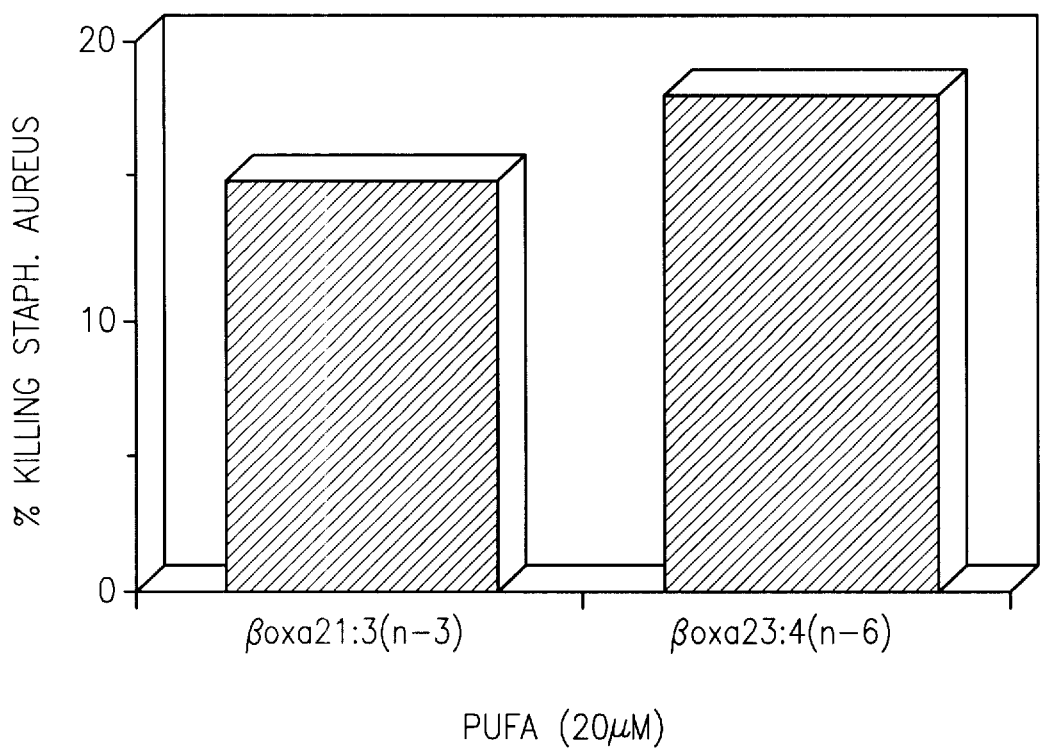
FIG. 8 shows the enhancement of neutrophil mediated killing of *Staph aureus* by fatty acids.
Figure 9A:
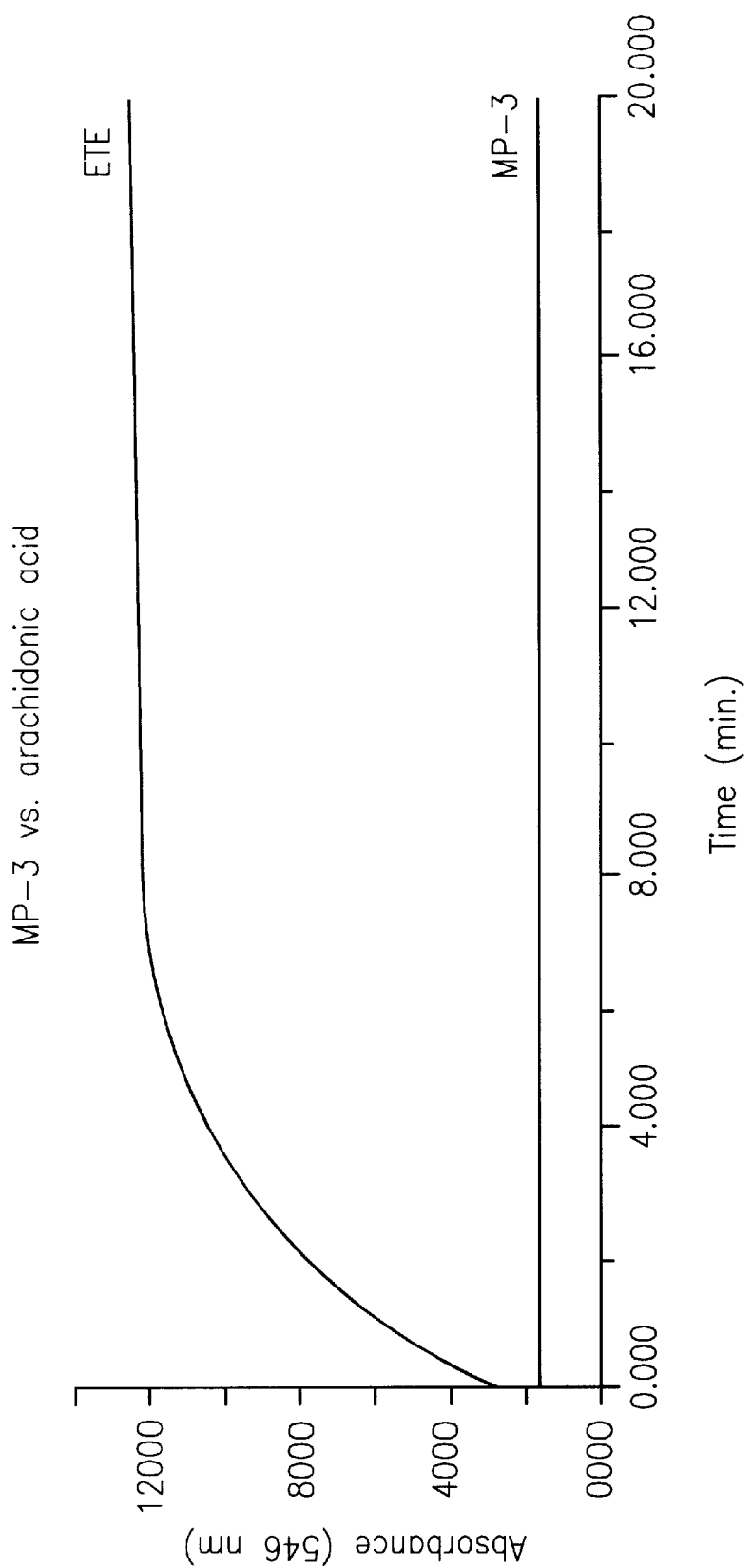
FIG. 9(a) shows the comparative abilities of arachidonic acid and β-oxa 23:4 (n-3) to undergo β oxidation
Figure 9B:
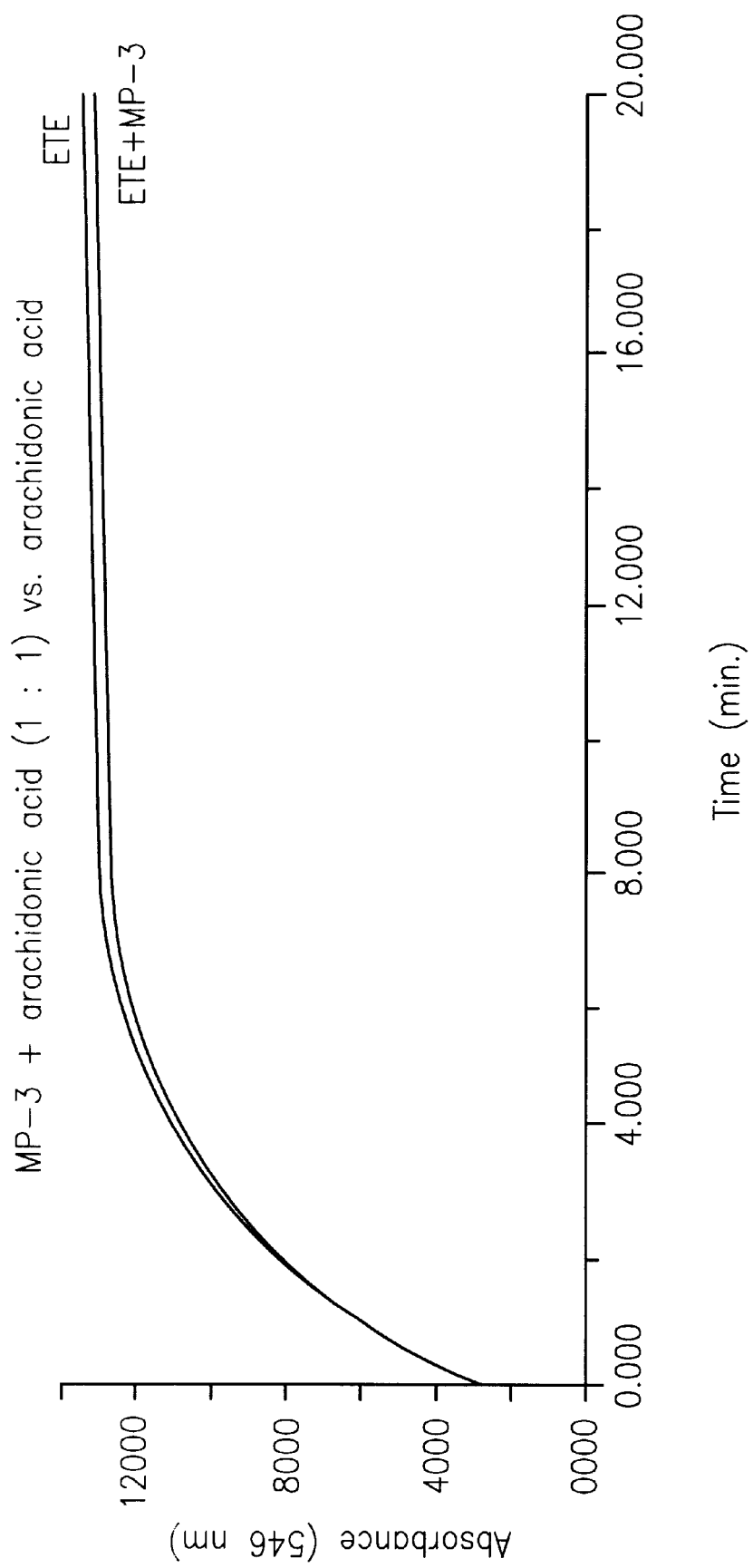
FIG. 9(b) shows that the compound does not inhibit β-oxidation of arachidonic acid and hence is unlikely to interfere with normal cellular metabolism.

In a similar fashion other naturally occurring unsaturated fatty acids (eg 22:6 (n-3)), and modified fatty acids such as FIGS. 1o–1x (Y=H) and related compounds prepared by elaboration of acids other that arachidonic acid can be used to prepare hydroperoxy, hydroxy and peroxy derivatives FIGS. 1o–1x (Y=OOH. OH. OOR), analogous to FIGS. 1b–1n, where the substitution pattern is determined by the allyic oxidation. The acids FIG. 1o and FIG. 1p(Y=H) can be prepared by aldol condensation of the corresponding aldehyde of FIG. 1a and FIG. 1p can also be prepared via a Wittig reaction of the same aldehyde or the corresponding halide, while the acid FIG. 1q can be prepared via a Wittig reaction of the corresponding C19 aldehyde or halide. The acid FIG. 1r can be prepared by aldol condensation of a corresponding ester of FIG. 1a, while FIGS. 1s–1x are obtained by ether or thioether synthesis, through nucleophilic substitution or metal catalysed coupling reactions, and the thioethers FIGS. 1v–1x can be oxidised to the corresponding sulphoxides and sulphones. The amino acid derivatives FIG. 1y and FIG. 1z can be obtained by coupling the corresponding fatty acid (FIG. 1a) and glycine and aspartic acid respectively.

Synthesis of Hydroxy β-oxa Fatty Acids

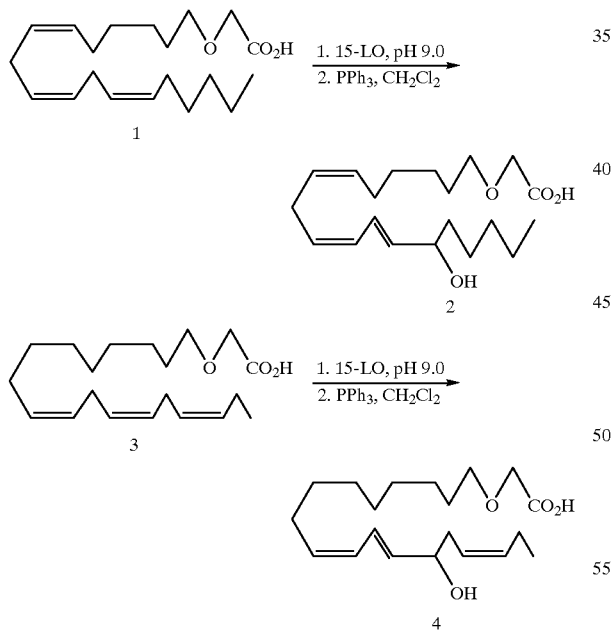

REAGENTS

β-oxa Fatty Acids (1,3)—synthesized from the corresponding fatty alcohols by rhodium acetate catalysed coupling with diazoacetate esters.
Triphenylphosphine - Aldrich Chemical Company.
Potassium Dihydrogen Orthophosphate - Ajax Chemicals.
Soybean 15-Lipoxygenase - Aldrich Chemical Company.
All solvents were distilled prior to use.

Preparative layer chromatographies were performed on Merck Silica Gel 60 $PF_{254}$ containing gypsum: Art 7749.

PROCEDURE

Hydroxy β-oxa Fatty Acids 2 and 4

The relevant fatty acid, 1 and 3, (ca. 50 mg) was dissolved in phosphate buffer (0.1 M. pH=9.0, ca. 45 ml) at 30° C. Soybean 15-lipoxygenase (ca. 8 mg) in phosphate buffer (ca. 5 ml) was added and oxygen was bubbled through the stirred solution for 10 min. Triphenylphosphine (ca. 50 mg) was added in dichloromethane (ca 50 ml) followed by hydrochloric acid (0.2 M, ca 20 ml) and the solution was stirred at 0° C. for 20 min. The crude reaction mixture was extracted with dichloromethane and the resulting extract was concentrated under a stream of dry nitrogen. The residue was purified by preparative layer chromatography on silica, eluting with ethyl acetate/hexane/acetic acid (80:20:0.1), to afford the respective hydroxy β-oxa fatty acid, 2 or 4, as an oil Z,Z,E-(13-Hydroxy-6,9,11-octadecatienyloxy)acetic acid (2)

[16′—OH—β-oxa 21:3(n6)]

$^1$H n.m.r. (300 MHz, $CDCl_3$) δ 0.89 (3H, t, J 6.8 Hz, C18′—$H_3$), 1.25–1.45 (10H, m, C3′—$H_2$, C4′—$H_2$, C15′—$H_2$, C16′—$H_2$, C17′—$H_2$), 1.59–1.73 (2H, m, C2′—$H_2$), 2.01–2.12 (4H, m, C5′—$H_2$, C14′—$H_2$), 2.81 (2H, t, J 5.8 Hz, C8′—$H_2$), 3.52–3.60 (2H, m, C1′—$H_2$), 4.10 (2H, s, C2–$H_2$), 4.20 (2H, dt,J 6.0, 6.7 Hz. C13′—H) 5.29–5.45 (3H, m, C6′—H, C7′—H, C9′—H), 5.70 (1H, dd, J 6.7 15.2 Hz). C12′—H) 5.99 (1H, dd, J 10.9 Hz. C10′—H) 6.55 (1H, dd, J 10.9, 15.2 Hz, C11′—H)

Z,E,Z-(13-Hydroxy-9, 11, 15-octadecatrienyloxy)acetic acid (4)

[16′—OH—β-oxa 21:3(n-6) ]

$^1$H n.m.r. (300 MHz, $CDCl_3$( δ 0.95 (3H, t, J 7.6 Hz. C18′—$H_3$), 1.17–1.40 (10H, m, C3′—$H_2$, C4′—$H_2$, C5′—$H_2$, C6′—$H_2$, C7′—$H_2$), 1.48–1.63 (2H, m, C2′—$H_2$), 1.99–2.12 (2H, m, C8′—$H_2$(, 2.13–2.22 (2H, m, C14′—$H_2$) 2.28–2.37 (2H, m, C17′—$H_2$), 3.44–3.50 (2H, m, C1′—$H_2$), 3.80–3.92 (2H, s, C2′—$H_2$), 4.14–4.20 (1H, dt, J 6.4, 14.9 Hz, C13′—H), 5.30–5.60 (3H, m, C9′—H, C15′—H, C16′—H), 5.67 (1H, dd, J 6.4, 14.9 Hz, C12′—H), 5.95 (1H, dd, J 11.1, 11.1 Hz. C10′—H), 6.49 (1H, dd, J 11.1, 14.9 Hz C11′—H)

Effect of novel fatty acids on the action of Acyl-CoA-Oxidase,

β-oxidation of fatty acids

β-oxidation is the main oxidative metabolic fate of fatty acids (1), the net process being characterized by the degradation of the fatty acid carbon chain by two carbon atoms with the concommitant production of equimolar amounts of acetyl-coenzyme A (4) (Scheme 1).

Scheme 1

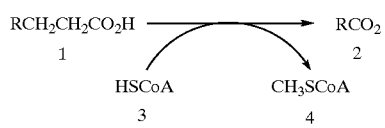

Acyl-CoA-oxidase

The first step in the β-oxidation pathway is controlled by acyl-CoA oxidase. In peroxisomes, acyl-CoA oxidase catalyses the reaction of acyl-coenzyme A thioesters with oxygen to produce enoyl-coenzyme A thioesters. In the presence of peroxidase enzyme the concomitant production of hydrogen peroxide is cycled back to oxygen with the net generation of one mole of water for each mole of acyl-coenzyme A thioester oxidized.

Novel fatty acids

Fatty acids bearing a blocking group at the β-position were anticipated as being inert to the usual course of β-oxidation. Novel fatty acids thus bearing a heteroatom at the β-position have been synthesised. The compounds used in the current investigation were arachidonyloxyacetic acid [β-oxa 23:4(n-6)], gamma linolenyloxyacetic acid [β-oxa 21:3(n-6)], linolenyloxyacetic acid [β-oxa 21:3(n-3)] and arachidonylthioacetic acid [β-thia 23:4(n-6)]. The oxidation of arachidonyl-thiopropionic acid [γ-thia 22:4(n-6)] was also investigated in order to assess the effect of a blocking group of the γ-position of a fatty acid upon β-oxidation.

Acyl-Co-A Oxidase assay

Acyl-CoA oxidase from Arthrobacter species is available from Boehringer Mannheim in stabilized tablet form and is commonly used together with acyl-CoA synthetase for the measurement of free acids in serum or plasma.

Assay principle

Free fatty acids are, in the presence of the enzyme acyl-CoA synthetase (acyl CS), converted by adenosine-5'-triphosphate (ATP) and coenzyme A (CoA) into acyl-coenzyme A (acyl-CoA,) resulting in adenosine-5'-monophosphate (AMP) and pyrophosphate being produced.

Acyl-CoA reacts with oxygen ($O_2$) in the presence of acyl-CoA-oxidase (ACOD) to form 2,3-enoyl-coenzyme A (enoyl-CoA.) with the generation of hydrogen peroxide.

The resulting hydrogen peroxide ($H_2O_2$) converts 4-aminoantipyrine (4-AA) and 2,4,6-tribromo-3-hydroxybenzoic acid (TBHB) into a red dye in the presence of peroxidase (POD). The dye is measured in the visible region at 546 nm.

Assay procedure
Wavelength: 546 nm
Micro Cuvette: 1 cm light path
Temperature: 25° C. (±1° C.)
Assay volume: 1.15 ml
Measurement of reaction mixtures against air Pippetted into cuvette:
1.00 ml reaction mixture:
$KH_2PO_4$ (87 mmol/l), $Mg^{2+}$(1.3 mmol/l),
ATP (1.5 mmol/l), CoA (0.26 mmol/l), POD
(21.7 kU/l), Acyl CS (165 U/l).
0.05 ml sample solution of free fatty acid(s).
[for blank assay 0.05 ml of distilled water was substituted]
Sample was mixed and tempereteted at 25__C. for approx. 10 min.
Following this, addition of:
0.05 ml N-ethyl maleinamide solution: (0.86 mmol/l)
Absorbance (A1) of solution was measured at 546 nm followed by the addition of:
0.05 ml ACOD solution: (8.7 kU/l).
At t=10 seconds after the addition of ACOD to the reaction mixture the change in visible absorption of the solution at 546 nm was measured for 20 min.
Assay calibration/authenication
Sample concentration dependance
Arachidonic acid (20:4(n-6), 10) was assayed at the following concentrations:
4.3 mM, 2.1 mM, 0.99 mM, 0.49 mM, 0.25 mM and 0 mM (blank assay).
As per FIG. 1 the assay shows rate dependance on the concentration of fatty acid.

Enzyme (ACOD) concentration dependance

A sample solution of arachidonic acid (20:4(n-6), 10) at a concentration of 0.99 mM was assayed using acyl-CoA oxidase concentrations as follows:
200 kU/l, 100 kU/l and 50 kU/l.
As per FIG. 2 the assay shows rate dependance on the concentration of enzyme (ACOD).

Assay of novel fatty acids

Solutions of the novel compounds at concentrations of 1.0 mM, 1.0 mM, 1.0 mM, 1.0 mM and 1.1 mM respectively were assayed using an acyl-CoA oxidase concentration of 100 kU/l.

As per FIGS. 3–6 the assay indicates that the β-oxa compounds and the β-thia compounds respectively, are not substrates for acyl-CoA oxidase (FIG. 11A).

Effect of novel compounds on arachidonic acid metabolism by Acyl-CoA oxidase

Sample solutions containing equimolar concentrations of arachidonic acid (10) and each of the novel compounds were assayed using an acyl-CoA oxidase concentration of 100 kU/l.

The assay shows that the novel compounds have no effect on the uptake of aracludonic acid by acyl-CoA oxidase.

Further, samples containing novel compounds and arachidonic acid (10) at relative concentrations of 4:1 and 16:1 were assayed and indicated no appreciable effect on the uptake of arachidonic acid by acyl-CoA oxidase (not shown).

Covalent Coupling of Fatty Acids to Amino Acids

Polyunsaturated fatty acid (1.80 mmol), HOSu [0.41 g, 3.60 mmol] and the amino acid t-butyl ester [3.60 mmol] were dissolved together in dimethylformamide [3mL] and the mixture cooled in ice bath. Dicyclohexylcarbodiimide (0.44 g, 2.16 mmol) in DMF (0.3 mL) and N-methylmorpholine (0.73 g, 7.20 mmol) were added. The mixture stirred for 20 hours, after which time some unreacted polyunsaturated fatty acid remained. More DCC (0.10 g) was added and the mixture stirred for further 20 hours. DCU was filtered off and the product isolated by reversed phase HPLC. The purified product was concentrated to an oil and trifluoracetic acid (30 mL) as added. After an hour stirring, the trifluoroacetic acid was evaporated to leave the product as a brown oil which was redissolved in $CH_3CN$ (6 mL) and purified by reversed phase HPLC. The pure fractions obtained were combined, concentrated and lyophilised (in t-butanol) to leave the product as a brown oil.

TABLE 1

DIRECT ANTIMALARIAL ACTIVITY OF NOVEL FATTY ACIDS

| COMPOUND | EC50 ($\mu$M) |
| --- | --- |
| β-oxa 21.3 (n-6) | <30 |
| β-oxa 21:3 (n-3) | 30 |
| β-oxa 21:4 (n-3) | 40 |
| β-thia 21.3 (n-6) | 30–50 |
| β-thia 21:3 (n-3) | 30–35 |
| β-oxa 25.6 (n-3) | <60 |
| γ-thia 22.0 (n-5) | 45 |
| γ-thia 22.3 (n-6) | 45 |
| β-oxa 23.4 (n-6) | <30 |
| β-thia 23.4 (n-6) | 15–30 |
| γ-thia 24.4 (n-6) | 15 |
| β-thia 25.5 (n-3) | 25 |
| α-carboxymethyl-β-thia 23.4 (n-6) | 50 |
| 16-OH-β-oxa 21:3 (n-6) | 50 |
| 16-OH-β-oxa 21:3 (n-3) | 40 |

TABLE 2

FATTY ACID STIMULATED NEUTROPHIL-MEDIATED ANTI-MALARIAL ACTIVITY

| COMPOUND | % INHIBITION RELATIVE TO 22:6 AT 16 µM |
|---|---|
| β-oxa 21:3 (n-3) | 45 |
| β-oxa 21.4 (n-3) | 85 |
| β-thia 21:3 (n-6) | 85 |
| β-thia 21:3 (n-3) | 73 |
| β-thia 23:4 (n-6) | 150 |
| γ-thia 24.4 (n-6) | 91 |
| β-thia 25.6 (n-3) | 47 |
| 16-OH-β-oxa 21:3 (n-6) | 33 |

TABLE 3

EFFECT OF MP8.MP11.MP14 ON KI CHLOROQUINE RESISTANT *P. FALCIPARUM*

| COMPOUND | % GROWTH INHIBITION |
|---|---|
| CHLOROQUINE | 12.4 |
| β-thia 23:4 (n-6) | 97 |
| γ-thia 24.4 (n-6) | 97 |
| β-thia 25.6 (n-3) | 98 |

TABLE 4

EFFECT OF FATTY ACIDS ON MITOGEN-INDUCED PERIPHERAL BLOOD MONONUCLEAR CELL PROLIFERATION

| COMPOUND | % INHIBITION OF INDUCED PROLIFERATION AT 20 µM PUFA |
|---|---|
| β-oxa 21:3 (n-6) | 17 |
| β-thia 21.3 (n-3) | 28 |
| β-thia 25.6 (n-3) | 97 |
| 18-OH-β-oxa 21.3 (n-6) | 50 |

TABLE 5

EFFECT OF PUFA ON PHA-INDUCED TNFα PRODUCTION

| COMPOUND | % INHIBITION OF CYTOKINE PRODUCTION (PUFA AT 20 µM) |
|---|---|
| β-oxa 21:3 (n-6) | 38 |
| β-oxa 21:3 (n-3) | 39 |
| β-thia 21:3 (n-6) | 17 |
| β-thia 21:3 (n-3) | 17 |
| γ-thia 22.3 (n-6) | 41 |
| γ-thia 22.3 (n-3) | 25 |
| β-oxa 23.4 (n-6) | 25 |
| β-thia 23.4 (n-6) | 35 |
| γ-thia 24.4 (n-6) | 34 |
| β-thia 25.5 (n-3) | 90 |
| 16-OH-β-oxa 21:3 (n-6) | 71 |
| 16-OH-β-oxa 21:3 (n-3) | 68 |

TABLE 6

EFFECT OF PUFA ON *STAPH AUREUS* INDUCED INTERFERON γ PRODUCTION BY PERIPHERAL BLOOD MONONUCLEAR CELLS

| COMPOUND | % INHIBITION (PUFA AT 20 µM) |
|---|---|
| β-oxa 21:3 (n-6) | 89 |
| β-thia 21:3 (n-6) | 45 |
| β-oxa 25.6 (n-3) | 44 |
| β-oxa 23.4 (n-6) | 89 |
| β-thia 23.4 (n-6) | 64 |
| β-thia 25.6 (n-6) | 96 |
| 16-OH-β-oxa 21:3 (n-6) | 77 |
| 16-OH-β-oxa 21:3 (n-3) | 65 |

What is claimed is:

1. A polyunsaturated fatty acid compound having antimalarial and/or neutrophil stimulatory activity, the polyunsaturated fatty acid containing 18–25 carbons and 1–6 double bonds and wherein the polyunsaturated fatty acid compound has one or two substitutions selected from the group consisting of β oxa, γ oxa, β thia and γ thia.

2. A polyunsaturated fatty acid compound as claimed in claim 1 in which the polyunsaturated fatty acid compound includes a further substitution selected from the group consisting of hydroxy, hydroperoxy, peroxy, carboxymethyl substitutions or attached to an amino acid.

3. A polyunsaturated fatty acid compound as claimed in claim 1 in which the polyunsaturated fatty acid compound contains 20–235 carbon atoms and 3–6 double bonds.

4. A polyunsaturated fatty acid compound as claimed in claim 1 in which the polyunsaturated fatty acid compound is an n-3 to n-6 fatty acid.

5. A polyunsaturated fatty acid compound as claimed in claim 1 in which the polyunsaturated fatty acid compound is 21 carbons with 3–4 double bonds containing a β oxa or β thia substitution.

6. A polyunsaturated fatty acid compound as claimed in any one of claims 1 to 4 in which the polyunsaturated fatty acid compound is 22 carbon atoms with 3–4 double bonds containing a γ thia or β oxa substitution.

7. A polyunsaturated fatty acid compound as claimed in any one of claims 1 to 4 in which the polyunsaturated fatty acid compound is 23 carbons with 3–4 double bonds containing a β thia substitution.

8. A polyunsaturated fatty acid compound as claimed in any one of claims 1 to 4 in which the polyunsaturated fatty acid compound is 24 carbons with 3–4 double bonds containing a γ thia substitution.

9. A polyunsaturated fatty acid compound as claimed in any one of claims 1 to 4 in which the polyunsaturated fatty acid compound is 25 carbons with 3–6 double bonds containing a β oxa substitution.

10. A polyunsaturated fatty acid compound as claimed in claim 1 in which the polyunsaturated fatty acid compound is 25 carbons with 3–6 double bonds containing a β thia substitution.

11. A polyunsaturated fatty acid compound as claimed in claim 1 in which the polyunsaturated fatty acid compound has a ω hydroxy substitution.

12. A polyunsaturated fatty acid compound as claimed in claim 1 in which the polyunsaturated fatty acid compound has 23 carbons, 3–6 double bonds, β thia and α-carboxymethyl group.

13. A polyunsaturated fatty acid compound as claimed in claim 1 in which the polyunsaturated fatty acid compound is covalently attached via the carboxy terminus to an amino acid.

14. A polyunsaturated fatty acid compound as claimed in claim 13 in which the polyunsaturated fatty acid compound is covalently attached to aspartic acid or glycine.

15. A method of producing an unsaturated oxa substituted fatty acid comprising reacting an unsaturated fatty acid alcohol with a carbene such that the carbene is inserted in the O—H bond of the alcohol.

16. A method as claimed in claim 15 in which the unsaturated fatty acid alcohol contains 18–25 carbon atoms and 1–6 double bonds.

17. A method as claimed in claim 15 in which the carbene is synthesized via rhodium acetate catalysed of a diazo compound.

18. A method as claimed in claim 15 in which an unsaturated β oxa substituted fatty acid is produced.

19. A method of treating inflammation in a subject, the method comprising administering to the subject a therapeutically effective amount of an anti-inflammatory composition comprising at least one hydroxy, hydroperoxy, or peroxy derivative of a polyunsaturated fatty acid having a carbon chain of 18 to 24 carbon atoms and having 1–6 cis or trans double bonds.

20. A method as claimed in claim 19 in which the poly unsaturated fatty acid contains oxygen or sulphur atoms within the carbon chains as oxa or thia derivatives.

21. A method as claimed in claim 19 in which the polyunsaturated fatty acid is selected from the group consisting of the C20:4n-6 (5,8,11,14-eicosatetraenoc acid). C20:5n-3 (5,8,11,14,17-eicosapentaenoic), C22:6n-3 (4,7, 10,13,16,19-docosahexaenoic acid) and arachidonic acid.

22. Method for treating rheumatoid arthritis or multiple sclerosis in a patient in need of such treatment, said method comprising the step of administering an effective amount of a polyunsaturated fatty acid as claimed in claim 1.

* * * * *

UNITED STATES PATENT AND TRADEMARK OFFICE
CERTIFICATE OF CORRECTION

PATENT NO. : 6,376,688 B1
DATED : April 23, 2002
INVENTOR(S) : Ferrante et al.

It is certified that error appears in the above-identified patent and that said Letters Patent is hereby corrected as shown below:

<u>Title page,</u>
Item [73], under "Assignee", delete "Peptide Technology Limited, New South Wales (AU)" and insert -- Peptide Technology Limited and Women's and Children's Hospital Adelaide, New South Wales (AU) and Adelaide (AU), --.

<u>Column 20,</u>
Line 30, is amended to delete "20-235" and insert -- 20-25".
Line 33, is amended to delete "n-3to" and insert -- n-3 to --.

Signed and Sealed this

Fifth Day of November, 2002

Attest:

Attesting Officer

JAMES E. ROGAN
*Director of the United States Patent and Trademark Office*